United States Patent [19]
Klieman et al.

[11] Patent Number: 5,817,119
[45] Date of Patent: Oct. 6, 1998

[54] SURGICAL INSTRUMENT FOR ENDOSCOPIC AND GENERAL SURGERY

[75] Inventors: Charles H. Klieman, 79 Cypress Way, Rolling Hills Estates, Calif. 90274; John M. Stiggelbout, Sausalito; Bruce M. Schena, Menlo Park, both of Calif.

[73] Assignee: Charles H. Klieman, Newport Beach, Calif.

[21] Appl. No.: 671,820

[22] Filed: Jun. 25, 1996

Related U.S. Application Data

[63] Continuation of Ser. No. 295,352, Aug. 24, 1994, abandoned, which is a continuation of Ser. No. 95,739, Jul. 21, 1993, abandoned.

[51] Int. Cl.⁶ .......................... A61B 17/28; A61B 17/32
[52] U.S. Cl. .......................... 606/174; 606/170; 606/205
[58] Field of Search ........................ 606/205–208, 606/174, 170; 128/751

[56] References Cited

U.S. PATENT DOCUMENTS

| | | |
|---|---|---|
| 3,730,185 | 5/1973 | Cook et al. . |
| 3,888,004 | 6/1975 | Coleman . |
| 4,258,716 | 3/1981 | Sutherland ........................ 606/174 X |
| 4,320,761 | 3/1982 | Haddad . |
| 4,672,964 | 6/1987 | Dee et al. ............................ 128/305 |
| 4,688,555 | 8/1987 | Wardle ................................. 128/4 |
| 4,763,669 | 8/1988 | Jaeger . |
| 4,838,853 | 6/1989 | Parisi . |
| 4,861,332 | 8/1989 | Parisi . |
| 4,872,456 | 10/1989 | Hasson ................................ 128/321 |
| 4,877,026 | 10/1989 | de LaForcade . |
| 4,880,015 | 11/1989 | Nierman .............................. 128/751 |
| 4,940,468 | 7/1990 | Petillo . |
| 4,978,333 | 12/1990 | Broadwin et al. . |
| 4,986,825 | 1/1991 | Bays et al. . |
| 5,024,652 | 6/1991 | Dumenek . |
| 5,026,387 | 6/1991 | Thomas . |
| 5,112,299 | 5/1992 | Pascaloff . |
| 5,133,736 | 7/1992 | Bales, Jr. et al. ..................... 606/205 |
| 5,174,300 | 12/1992 | Bales et al. ...................... 606/174 X |
| 5,176,697 | 1/1993 | Hasson et al. ....................... 606/191 |
| 5,209,747 | 5/1993 | Knoepfler ............................. 606/16 |
| 5,224,954 | 7/1993 | Watts et al. ......................... 606/205 |
| 5,254,130 | 10/1993 | Poncet et al. ................... 606/205 X |
| 5,258,007 | 11/1993 | Spetzler et al. ................ 606/205 X |

(List continued on next page.)

FOREIGN PATENT DOCUMENTS

| | | |
|---|---|---|
| 0 577 423 A2 | 1/1994 | European Pat. Off. . |
| 0577423-A2 | 1/1994 | European Pat. Off. . |
| 2681775-A1 | 4/1993 | France . |
| 40 00 307 A1 | 7/1994 | Germany . |
| 43 07 539 A1 | 9/1994 | Germany . |
| 980703-A | 12/1982 | U.S.S.R. . |
| WO 91/02493 | 3/1991 | WIPO . |
| WO 92/14412 | 9/1992 | WIPO . |
| 007816 | 4/1993 | WIPO ............................... 606/205 |

OTHER PUBLICATIONS

Hospital Price List, effective Feb. 24, 1992, published by Ethicon, a Johnson & Johnson company.

Advertisement dated May of 1992 for Auto–Sector™ published by Omni–Tract Surgical.

*Primary Examiner*—Michael H. Thaler
*Attorney, Agent, or Firm*—Fish & Richardson P.C., P.A.

[57] ABSTRACT

A surgical instrument having a handle, barrel and working end effector tip is provided. The barrel is generally tubular, with one end being releasably connected to the handle. The end effector is moveably attached to the other end of the barrel, and may be positioned and operated independently through multiple linkage members connected to a motive power source housed in or attached to the handle. The instrument is operated and controlled by a microprocessor and multidimensional controller or electrical contacts included in the handle. In the preferred embodiment, the end effector is scissor-like, but other end effectors such as graspers, clamps, dissectors or needle drivers, with appropriate operating and linkage members, may be attached to the handle.

34 Claims, 23 Drawing Sheets

U.S. PATENT DOCUMENTS

| | | | |
|---|---|---|---|
| 5,275,615 | 1/1994 | Rose . | |
| 5,281,220 | 1/1994 | Blake | 606/205 X |
| 5,282,806 | 2/1994 | Haber et al. . | |
| 5,282,807 | 2/1994 | Knoepfler . | |
| 5,282,826 | 2/1994 | Quadri | 606/207 |
| 5,300,081 | 4/1994 | Young et al. . | |
| 5,308,358 | 5/1994 | Bond et al. | 606/205 |
| 5,314,445 | 5/1994 | Heidmueller et al. . | |
| 5,318,589 | 6/1994 | Lichtman | 606/205 |
| 5,330,502 | 7/1994 | Hassler et al. | 606/205 |
| 5,350,355 | 9/1994 | Sklar | 604/23 |
| 5,350,391 | 9/1994 | Iacovelli . | |
| 5,354,311 | 10/1994 | Kambin et al. | 606/205 |
| 5,368,606 | 11/1994 | Marlow et al. | 606/170 |
| 5,374,277 | 12/1994 | Hassler | 606/207 |
| 5,383,888 | 1/1995 | Zvenyatsky et al. | 606/205 X |
| 5,403,342 | 4/1995 | Tovey et al. | 606/205 |
| 5,536,251 | 7/1996 | Evard et al. | 604/93 |
| 5,582,617 | 12/1996 | Klieman et al. | 606/170 |

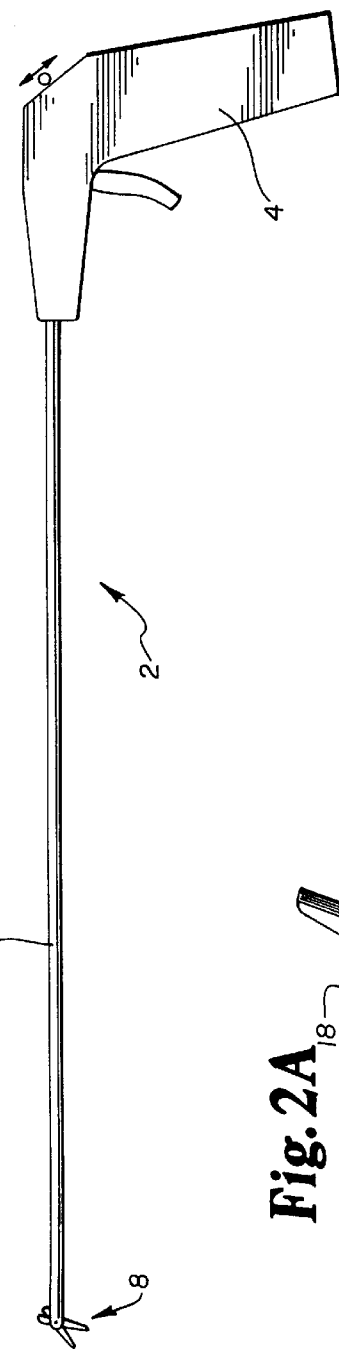
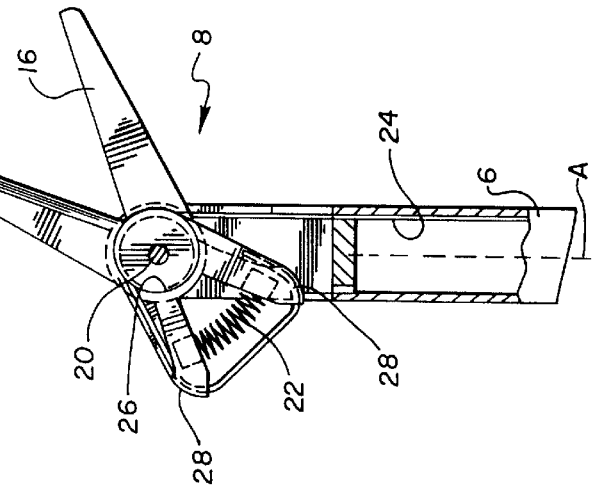
Fig. 1
Fig. 2A

Fig. 2B
Fig. 2C
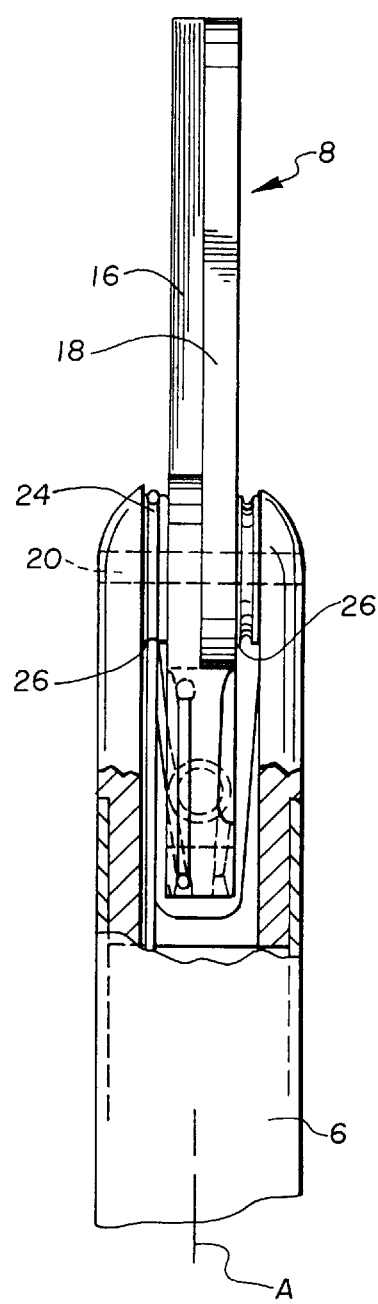
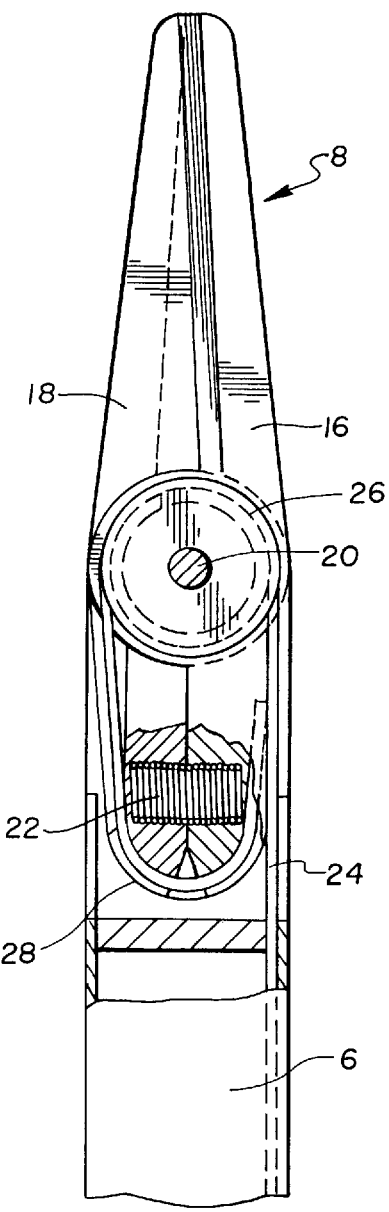

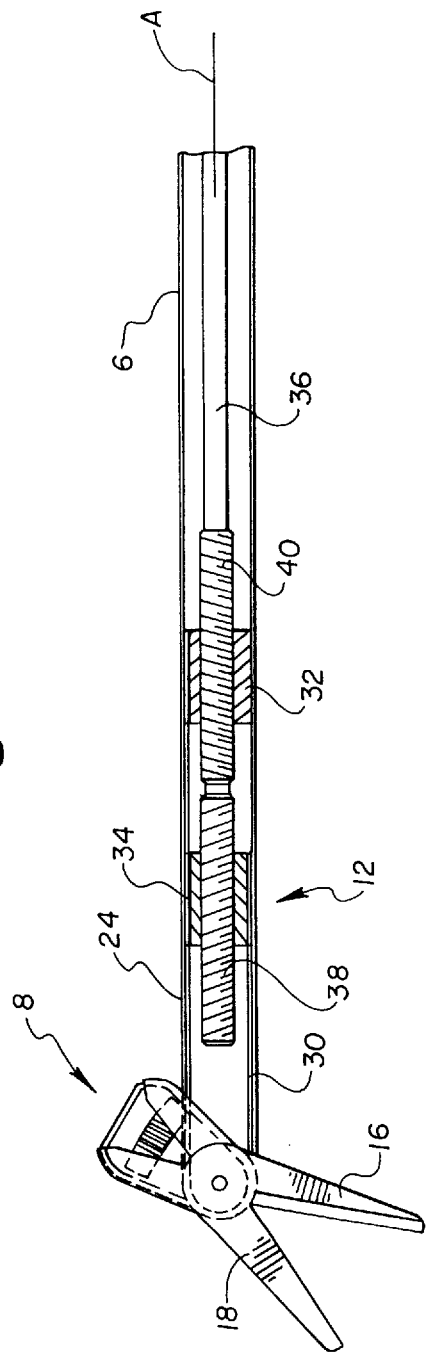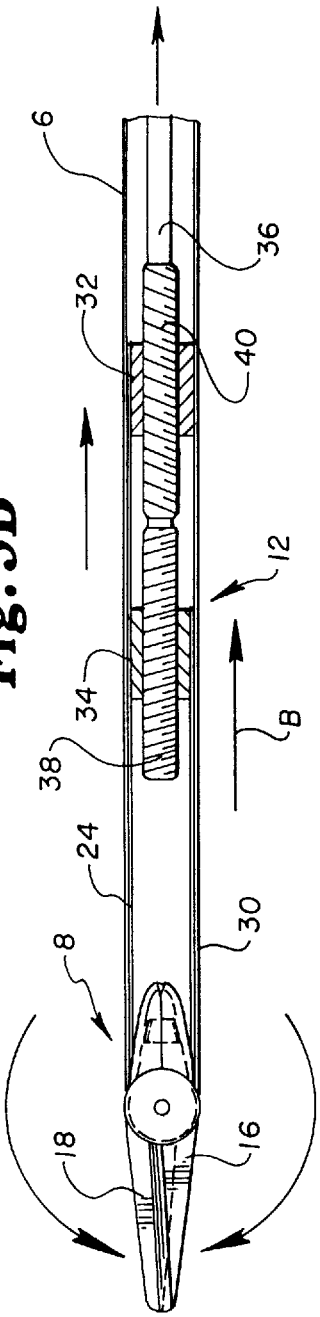

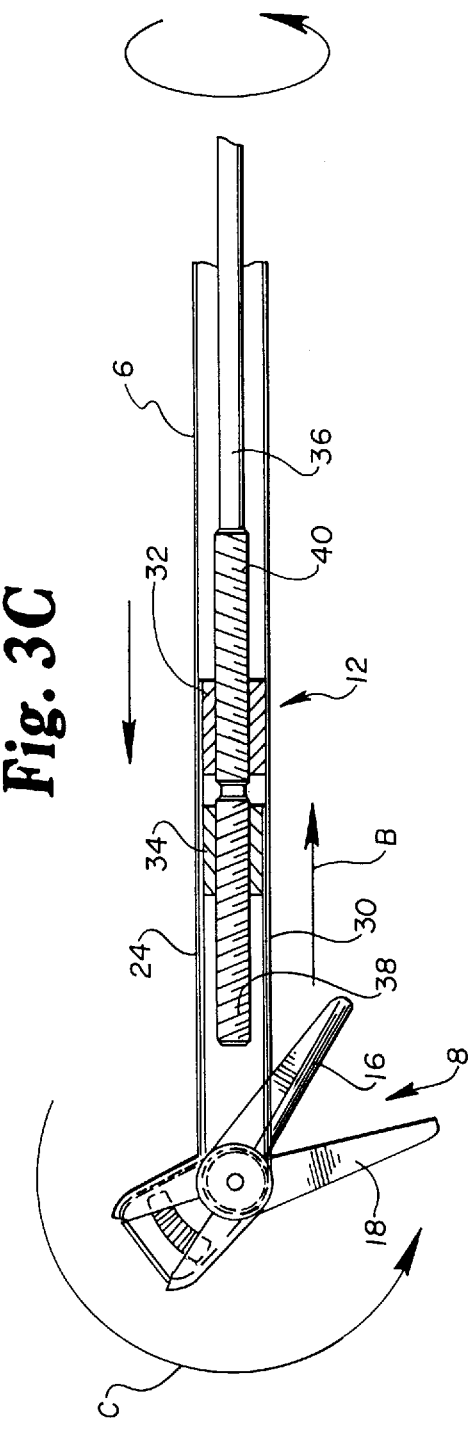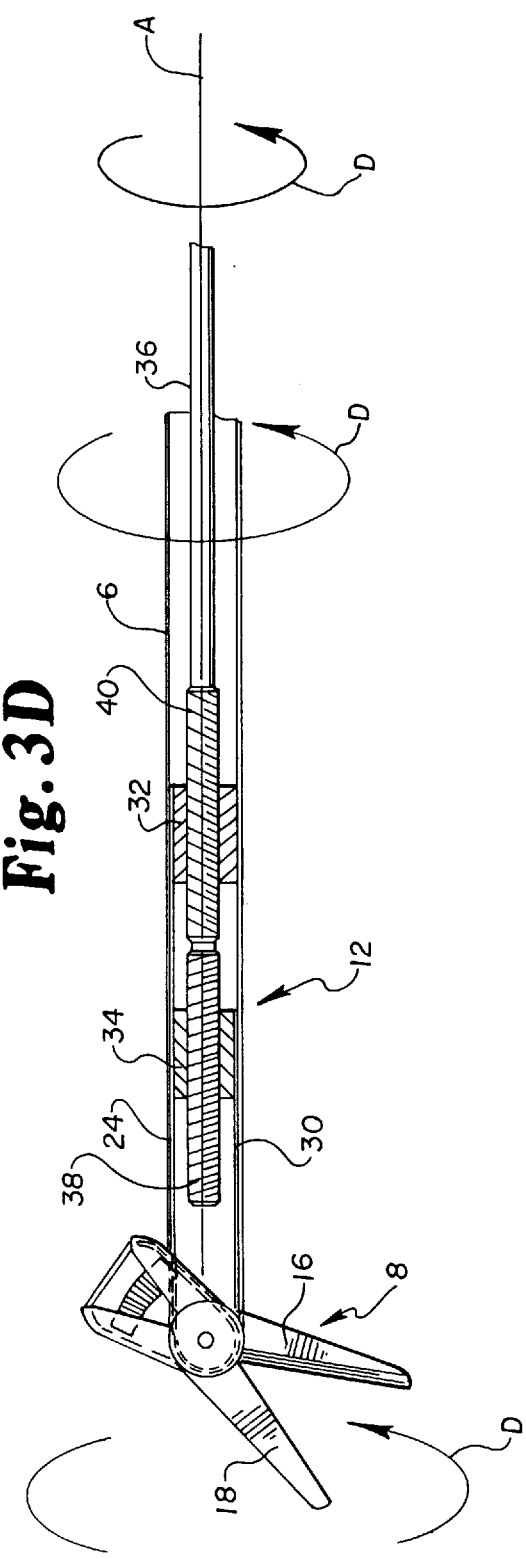

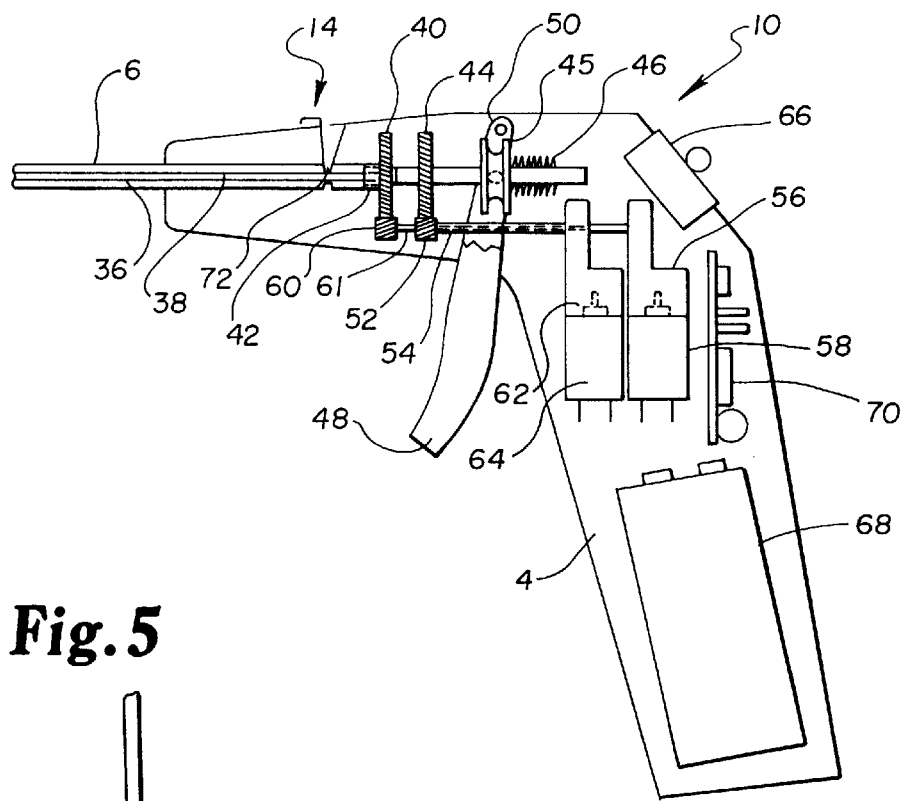
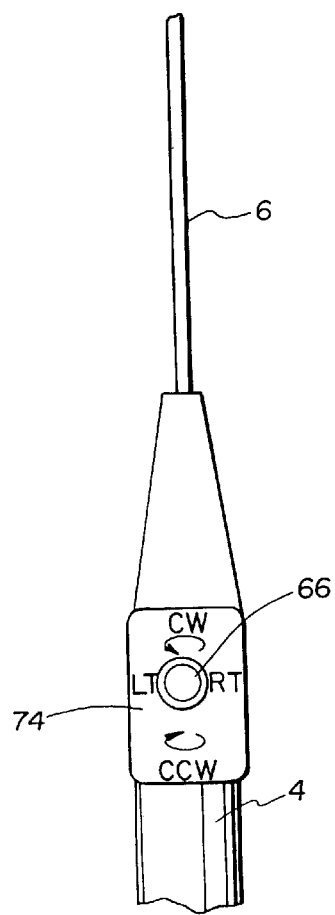

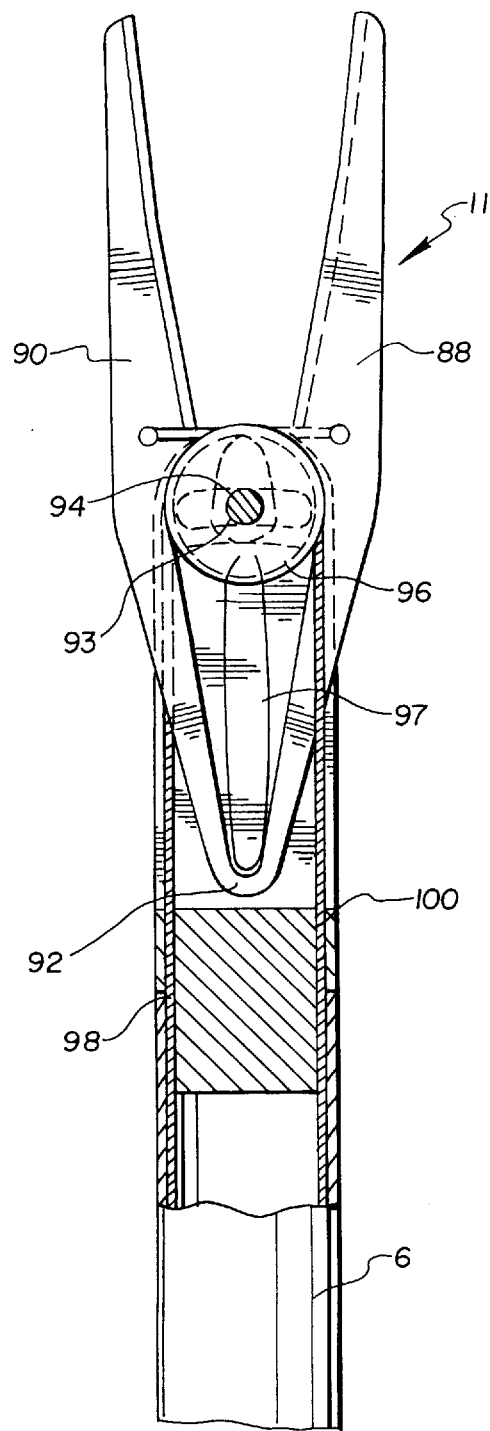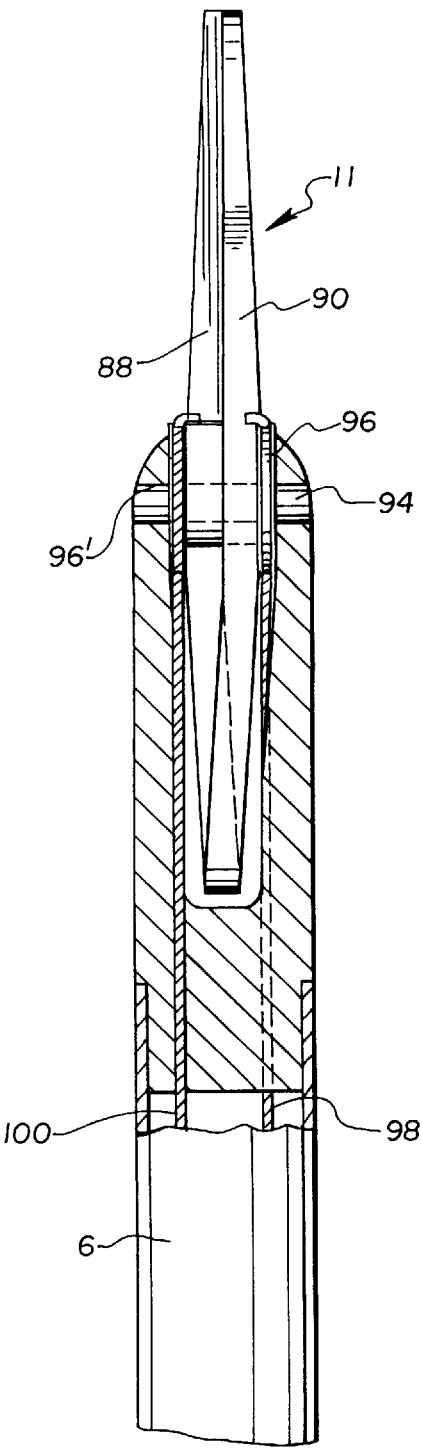
Fig. 7A
Fig. 7B

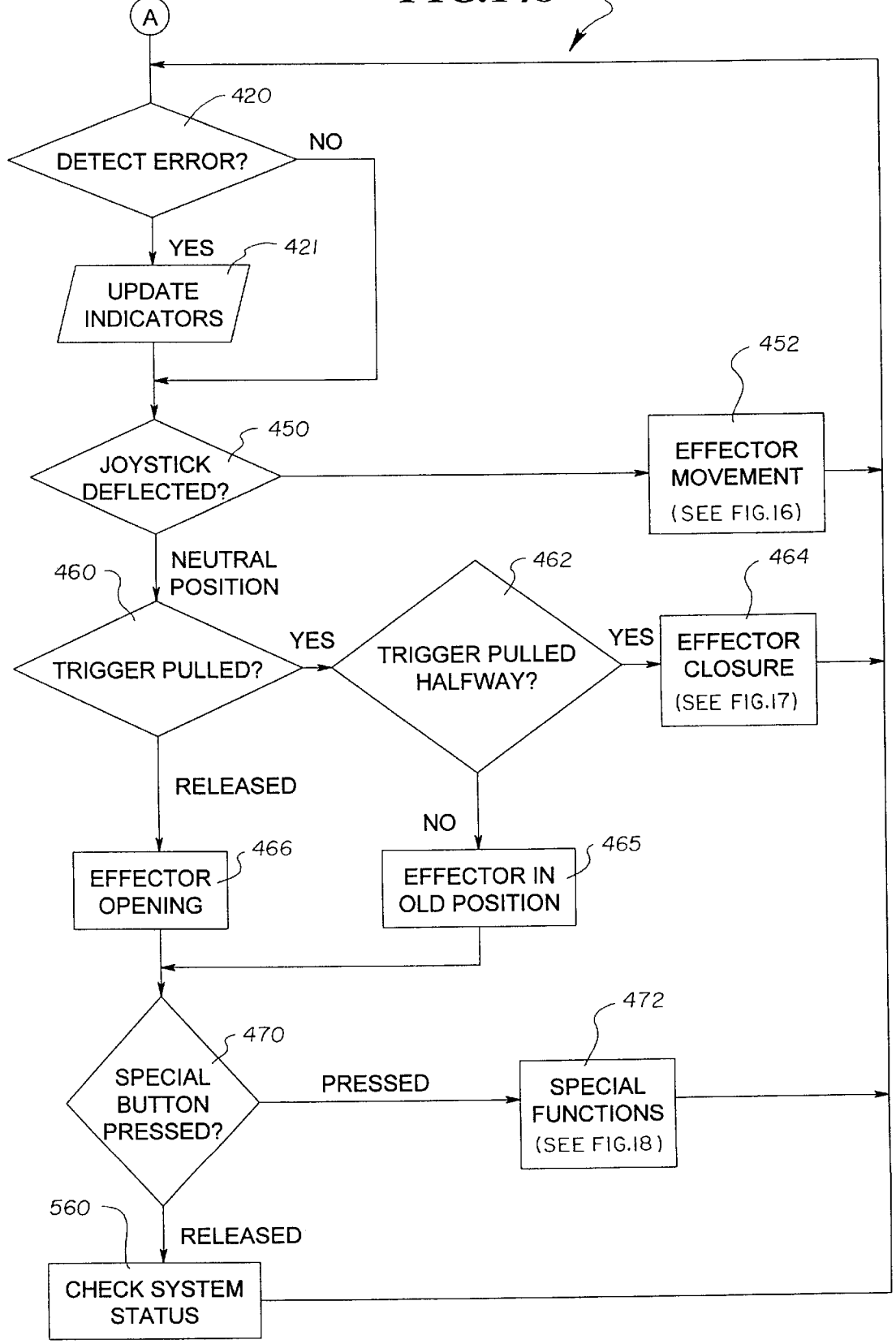

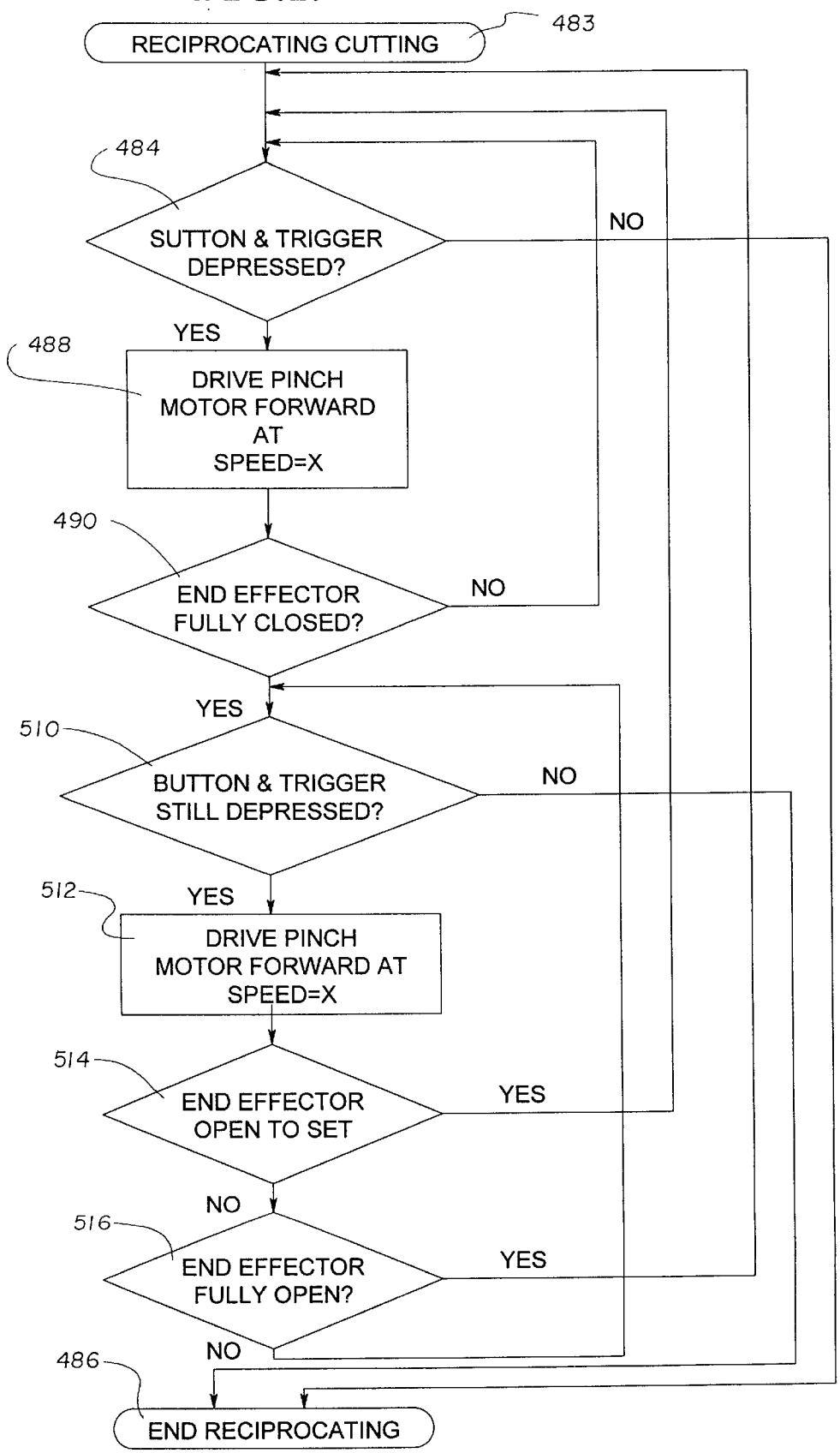

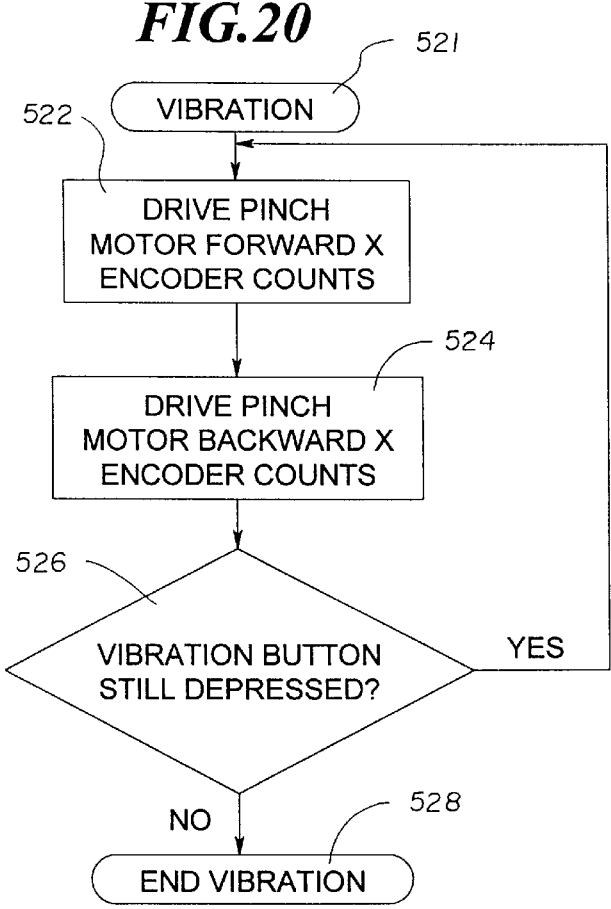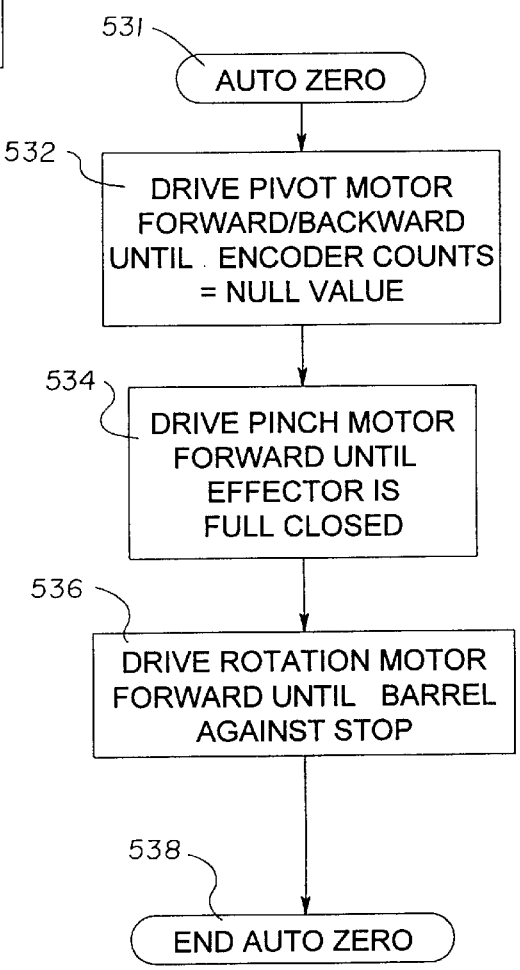

SURGICAL INSTRUMENT FOR ENDOSCOPIC AND GENERAL SURGERY

This is a continuation of application Ser. No. 08/295,352 filed Aug. 24, 1994, now abandoned, which is a continuation of application Ser. No. 08/095,739 filed Jul. 21, 1993, now abandoned.

The present invention relates generally to the field of surgical instruments. In particular, it relates to a surgical instrument for use in endoscopic surgical procedures, wherein the instrument, especially the end effector carried thereby, may be positioned and operated with one hand.

BACKGROUND OF THE INVENTION

Endoscopy (e.g., laparoscopy, thoracoscopy, arthroscopy, etc.) is a form of surgery that involves visualizing the interior of the body using an illuminating optical instrument, an endoscope. The endoscope and other surgical instruments are introduced into the body through small puncture orifices.

Endoscopic procedures typically are commenced by using a device known as a trocar. The trocar comprises a cannula or trocar sleeve (a hollow sheath or sleeve with a central lumen) and a sharp obturator received in the cannula. The trocar is used to penetrate the abdominal wall or chest. The obturator is withdrawn from the cannula after the intra-abdominal end of the trocar is in the abdominal cavity, and the cannula remains in the abdominal wall throughout the surgical procedure, allowing the introduction of surgical instruments. Trocars are available in different sizes, as are cannulae, to accommodate various instruments.

Endoscopy, in the form of laparoscopy, traditionally has been used almost exclusively for gynecological surgery. However, physicians specializing in other fields have begun to recognize the diagnostic and operative value of endoscopy.

The advantages of endoscopic surgery include: procedures may be performed on an outpatient basis; surgeons are given the opportunity to view intra-abdominal viscera without performing a laparotomy, a large incision of the abdominal wall; small puncture ports or wounds are created rather than large incisions, lessening trauma; incision sites for laparotomies may be determined accurately; patient and insurer medical costs are reduced by shorter hospital stays; and postoperative patient discomfort, with recovery times measured in days as opposed to weeks, is lessened.

Thus, there is a substantial interest in and need for providing task specific surgical instruments particularly adapted to general surgical procedures now being performed endoscopically. Because endoscopy, particularly laparoscopy, is an evolving specialty within the field of general surgery, currently available instruments inadequately meet the needs of laparoscopic surgeons.

Heretofore, surgical instruments designed specifically for endoscopic procedures generally take the form of a specialized implement (hereinafter called an end effector) fixedly attached to the distal end of a rigid shaft, with an operating linkage mechanism internal or external to that shaft. A handle attached to the opposite, proximal end of the shaft usually has an associated manual mechanism for operating the end effector, and a second mechanism to rotate the shaft and end effector. Generally, in order to fit through the small diameter ports or incisions, an instrument is designed for a single, dedicated, specialized purpose. Ideally, a surgeon selects instruments according to his preferences and according to the procedure at hand. However, because of the costs involved with using additional instruments and the time associated with removing one and inserting another, a surgeon is inclined to make do with the instruments of initial use even though another instrument may be more suitable for the immediate task.

Another significant limitation in the design of current instruments is that to reposition the end effector, a surgeon must use both hands; one hand to manipulate manually a thumbwheel or knob to rotate the shaft (and end effector), and one to hold the instrument. This means that a second instrument in use has to be released, or the assisting physician or nurse has to provide help.

U.S. Pat. Nos. 4,986,825 (to Bays et al.) and 5,133,736 (to Bales, Jr. et al.) disclose surgical instruments including end effectors, e.g., scissors, dissectors, cutting jaws, etc., attached to tubular members. However, neither patent discloses or teaches how to conveniently reposition an end effector relative to the rest of an instrument while the instrument is in use.

An even greater limitation stems from the fact that end effectors are fixedly attached to the distal end of the instrument shaft which passes through the endoscopic port. Because of this limitation in instrument design, correct placement of the port is crucial for direct access to the subject tissue or internal structure. Frequently, due to the fixed position of the end effector relative to the instrument shaft, additional laparoscopic ports or incisions must be created to allow a suitable instrument angle and access to the tissue of interest.

SUMMARY OF THE INVENTION

Accordingly, it is an object of the present invention to provide a surgical instrument which enhances surgeons' capability and dexterity, yet requires a minimum number of endoscopic ports.

The surgical instrument of the present invention comprises a handle grip, barrel and a working end effector tip. The barrel is generally tubular, with one end being releasably connected to the handle. The end effector is rotationally and pivotally attached to the other end of the barrel. The end effector may be, for example, scissor-like having two blades pivotally and rotationally connected to the distal end of the tubular barrel. The distal end of each of the blades of the scissor end effector is sharpened to allow shearing between the two blades as they pivot against one another. The blades cross over one another at a pivot point, and the opposite portions of each blade are configured as levers extending an equal distance in the proximal direction. Between these levers is a compression spring biasing the levers apart, thereby opening the cutting jaws. On the outside edges of these levers are grooves which extend around a radius on the proximal end of the levers. The grooves are polished and wide enough to accommodate a high modulus tensile cord which is free to slide back and forth. There are two cords, the first of which is attached to a first blade lever and crosses around the proximal end of the first blade lever into the groove in the second blade lever, along the outside edge of the second blade lever and over a pulley which is free to rotate around the same pivot as the scissor blades. A second cord is attached to the second blade lever and crosses around the proximal end of the second blade lever into the groove in the first blade lever, along the outside edge of the first blade and runs in the opposite direction around another pulley on the opposite side of the two blades. The free ends of the two cords lead inside the tubular barrel. These cords are kept in positive tension by the action of the spring between the lever end of the blades. Pulling one cord while releasing the other causes coordinated pivoting of the two blades. Pulling the two cords simultaneously causes coordinated closing of the blades. Rotating the tubular barrel causes axial rotation of the blades together with the pulleys and cords.

Coordinated movement of the two cords is achieved by the use of a threaded shaft mounted within the tubular barrel. The distal end of the internal shaft is threaded with a right-hand thread, followed by a left-hand thread, each to a length exceeding the total travel of the pull-cords described above. Two nuts (one threaded in right-hand orientation and the other in left-hand orientation) which are constrained from rotating, but can slide lengthwise inside the tube, are screwed onto the shaft. One of the above mentioned cords is attached to the first (distal end) nut while the second passes through a hole in the first nut and attaches to the second nut (proximal end). The threaded shaft, which can both rotate and slide axially inside the tubular barrel, is attached to a spline within the pistol grip handle. A cylindrical collar is also located within the handle and is attached to the shaft to allow engagement by a trigger mechanism to pull the shaft, together with the nuts and cords, in the proximal direction, thereby closing the scissor blades. Rotation of the shaft, by way of gears or pulleys engaging the spline, allows coordinated movement of the nuts, and thereby the cords, pivoting the scissor blades in either direction. Pivoting of the blades can be accomplished irrespective of the location of the shaft and state of closure of the blades, thereby allowing independence between the pivoting and rotation movements. Rotation of the shaft, and the resulting pivoting of the blades, may be produced manually, but incorporation of small gear-motors allows the use of a joystick-like control for an improved user interface and better usability.

Retraction of the threaded shaft and subsequent closure of the blades is accomplished either manually or automatically. In the manual embodiment, a set of levers, or linkages, is connected to a trigger-like handle attached to the pistol grip and is actuated by squeezing the hand closed. Manual closure offers direct tactile feedback to the user.

In the entirely electrically driven or powered embodiment, movement, specifically retraction, of the shaft is achieved with the aid of a geared motor or other source of motive power. The motor may be internal or external to the handle of the device, and an appropriately located power on/off switch, or switches, are associated with the handle. The capability of rapidly opening and closing the scissor blades in the powered embodiment is of great value in using the scissor-like end effector tip as a dissection instrument. This functionality is included in the invention by way of a separate motor and gearing means alternately causing partial retraction of the threaded shaft (thus partially closing the scissor blades) and release of the threaded shaft (thus opening the scissor blades). This reciprocating movement may be controlled by pressing a button on the handle.

In the preferred embodiment of the present invention, the end effector is a scissor-like tip, but a further feature of the invention is interchangeability of end effector tips. This interchangeability extends to the tubular barrel, the end-effector carried by thereby and associated mechanisms. In this alternative embodiment, the tubular barrel and shaft(s) are splined to allow engagement with gearing means within the handle. The retraction linkages or levers (which close the blades) are capable of being disconnected from the collar attached to the threaded shaft inside the tubular barrel. Replacement of the tip and barrel is accomplished by pressing a detent button mechanism on the handle, releasing one tip so that another tip of the same or a different type may be inserted.

Another object of the present invention is to provide an improved surgical device having an articulated end effector or instrument head enabling the surgeon to reach areas difficult to access during a general endoscopic procedure, particularly a laparoscopic or thoracoscopic procedure, quickly and conveniently without having to move or reposition the instrument as a whole.

Still another object of the present invention is to provide an instrument adapted to accept various working end effector tips, and to provide means, incorporating elongated, tensile linkage members, for positionally rotating, pivoting and operating the selected end effector. Generally, the different interchangeable end effector tips include those providing all pinching or grasping actions, and tips providing other movements at the distal end of the instrument.

Yet another object of the present invention is to provide an endoscopic instrument designed to pass through trocar sleeves or endoscopic ports of various sizes, including 5 mm trocar sleeves, thereby permitting its use in minimally invasive procedures.

The instrument of the present invention advantageously provides flexibility by including a family of instruments, through the use of a common handle and actuating drive mechanism, and different end effector tips, each connectable quickly and conveniently to the drive mechanism according to need. This inter-changeability gives the user the ability to change from one functional device to another quickly and easily while continuing to use a common handle with its associated motors, gears and controls. It also permits parts of the device to be disposable while making the most expensive parts reusable. A major advantage of the instrument is that the part of the device which penetrates the patient's body cavity will be new, sharp, and guaranteed sterile, while the rest of the device could be cleaned, sterilized, and reused. Of course, if justified by cost factors, the entire instrument may be disposable.

Still another object of the present invention is to provide an endoscopic instrument with an integrated microprocessor. An advantage of incorporating a microprocessor into the instrument of the present invention is that the logic can maintain accurate and repeatable positional control of the drive motors. Logic control may be useful in facilitating the following functions:

Reciprocating movements. Snipping or automatic cutting may be achieved by holding a control button, thereby causing the end effector blades to open and close cyclically and continuously. This type of function would be particularly useful for rapid sectioning of tissue. Several aspects of this action can be controlled independently by a microprocessor, including the degree of opening and closing, the rate of reciprocation, the closing force and the non-linear motion (either force or speed), i.e., fast movement at the beginning of a stroke, slow movement at the end or vice versa;

Vibration or wiggling of the tip. Movement or vibration in the plane of the blades is useful in the dissection of tissues. Such movement can be achieved by pressing a dedicated switch, driving an electro-mechanical actuator or motor forward and backward at a high rate of speed. Both the frequency and degree of such rotational motion can be regulated with accuracy by a microprocessor;

Proportional control. Accurate and repeatable control of the end effector tip is critical to a surgeon. It would be advantageous to make the rate of the pivoting of the end effector or rate of rotation of the barrel proportional to the offset of the multi-position "joystick" switch or proportional to the force with which an electromechanical switch is pressed. Similarly, as described above, the position of the multi-position joystick corresponds to the orientation of the end effector, i.e., control to the left and the end effector pivots to the left, etc.;

Zero position for retraction or insertion. A dedicated switch might be provided which when depressed, drives the end effector to a predetermined position. This is particularly useful to the surgeon because insertion or retraction from an endoscopic port requires that the end effector must be closed, i.e, in the straight ahead position. This is easily accomplished if logic control is provided to keep track of the motor position at all times; and Other functional and operational advantages. Incorporating a microprocessor into the instrument enables multi-functional switches to reduce the number of keys or buttons on the handle of the instrument. For example, the finger-operated trigger may close the blades proportionally unless another button is depressed in which case the motion is automatic and cyclical. Similarly, speed and force parameters may be changed with a use of a "shift" button. Status indicators, in the form of LED's or liquid crystal displays may be used to show information to the user. Battery regulation, in that electronic logic may be used to control the rate of charge and discharge of batteries, may be provided by a microprocessor.

The present invention has several additional important advantages over existing endoscopic surgical instruments beyond the capability to incorporate various end effector tips and articulate the selected end effector. Incorporation of electronically controlled motors and clutches gives additional flexibility to the user interface a surgeon uses to move the device in the desired directions. This interface may take the form of small slide switches, joysticks, knobs or buttons and electronic logic integrated into the handle or a remote interface controlled by a computer or other external device.

The above and other features, objects and advantages of the present invention will become more fully apparent and understood upon consideration of the following detailed description, in conjunction with the accompanying drawings and claims. It should be understood that the descriptions and drawings are for purposes of description and illustration only and are not intended as a definition of the limits of the invention.

BRIEF DESCRIPTION OF THE DRAWINGS

FIG. 1 is a left side elevational view of the present invention;

FIG. 2A is a fragmentary view of the distal end with parts broken away for clarity;

FIG. 2B is a fragmentary view of the distal end of the invention of FIG. 1, with parts broken away and rotated 90 degrees;

FIG. 2C is a fragmentary view of the distal end thereof with parts broken away;

FIG. 3A is a fragmentary side elevational view of the invention of FIG. 1, sectioned along the longitudinal axis of the instrument;

FIG. 3B is a view similar to that of FIG. 3A and, depicting an operational snipping movement of the end effector of the instrument of the present invention;

FIG. 3C is a view similar to that of FIG. 3A depicting rotational, positioning movement of the end effector;

FIG. 3D is a view similar to that of FIG. 3A showing revolving movement of the barrel and end effector;

FIG. 4 is a fragmentary left side elevational diagram of the proximal handle end of the present invention depicting the actuator mechanism thereof in assembly;

FIG. 5 is a fragmentary rear elevational view of the handle;

FIG. 7A is a fragmentary view of the distal end of a fourth alternate form of the invention with parts broken away;

FIG. 7B is a fragmentary view of the form of the invention of FIG. 7A, shown rotated 90 degrees and with parts broken away;

FIG. 14–23 are flow diagrams depicting the operating of the microprocessor controlled embodiment of the present invention, including FIG. 14 depicting the overall main operation and FIGS. 15–23 depicting sub-routines.

DETAILED DESCRIPTION OF THE DRAWINGS

Figure 2D:
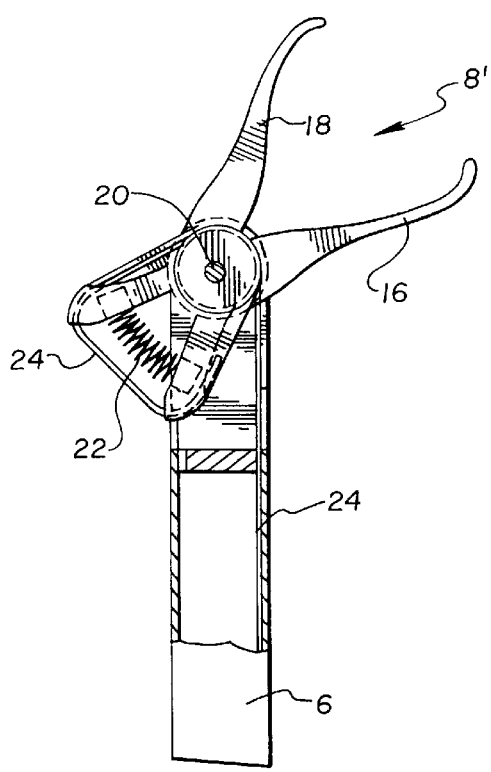
FIG. 2D is a fragmentary view of a first alternate form of the of the distal end of the present invention with parts broken away for clarity.

Referring to FIG. 1, the surgical instrument 2 of the present invention includes a handle 4, a tubular barrel 6 and end effector 8. As shown in FIG. 4, the handle 4 houses the operating mechanism 10, including motor mechanisms and associated gearing, batteries, control electronics and actuator switches as will be set forth in more detail herein below.

The tubular barrel 6 of the instrument 2 houses linkage means 12 (see, for example FIGS. 3A–D) for closing and rotating the end effector 8, rotating of the barrel 6 and, referring to FIG. 4., includes a disengagement detent mechanism 14 to allow removal of the barrel 6 from the handle 4. In FIG. 1 the end effector 8 is illustrated as a scissor-like working tip. However, the end effector 8 may be graspers, extractors, clamps, forceps and other devices useful during surgery. The barrel 6 and end effector 8 may be disposable or reusable.

Figure 2E:
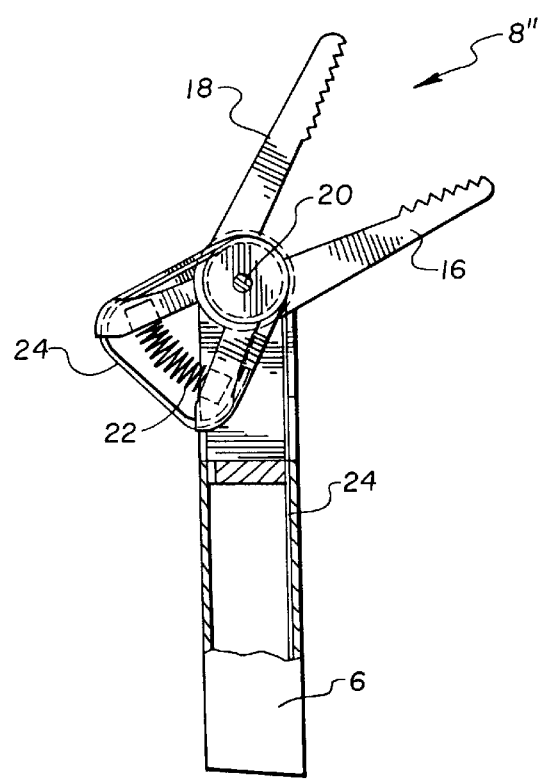
FIG. 2E is a fragmentary distal end view of a second alternate form of the distal end of the present invention with parts broken away.
Figures 6, 6A, 6B:
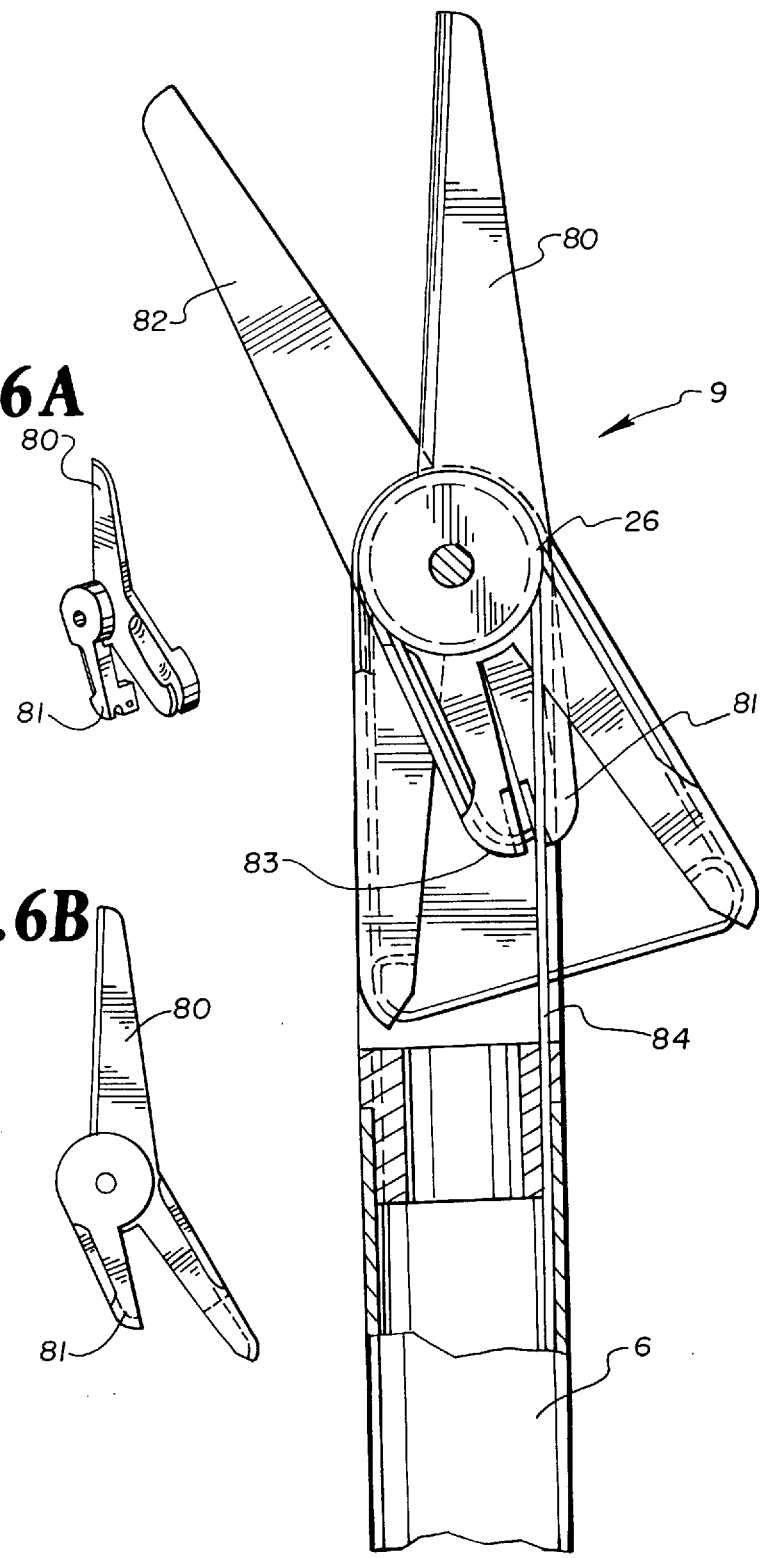
FIG. 6 is a fragmentary view of the distal end of a third alternate form of the invention with parts broken away.
FIG. 6A is a perspective detail view thereof.
FIG. 6B is a detail side elevational view thereof.

FIGS. 2A–C show enlarged views of the scissor-like end effector 8 and FIGS. 2D–E show enlarged views of alternative end effectors 8' and 8". In FIG. 2A the scissor end effector 8 is open and rotated 45° relative to the barrel 6. In the preferred embodiment, the scissor-like working end effector tip 8 is comprised of two blades 16 and 18 pivotally attached to the barrel tube 6 by way of pin 20. The blades 16, 18, as a pair, are rotatable 360° around pin 20 and each blade 16, 18 is rotatable 45° relative to the other blade from a fully closed position (FIG. 2C) to a fully open position (FIG. 2A). The blades 16, 18, as shown in FIG. 2C, are parallel to one another, each having an adjacent flat face, which, when the tip 8 is closed, creates a shearing edge. The two blades 16, 18 are biased toward the open position by a spring (or springs, not depicted) 22. Two control cords 24, 30, of which only one, cord 24, is shown in FIG. 2A–C for clarity, the other being substantially identical, are provided for closing the blades 16, 18 relative to one another and for pivoting the blades 16, 18 relative to the tubular barrel 6. The control cords 24 extend along the longitudinal axis (A in FIG. 2A) of the barrel 6, over a pulley 26, which is free to rotate independently around pin 20, and along the back of the butt or proximal end 28 of the blades 16, 18. A polished radius is machined in the proximal end 28 of both blades 16, 18, for receiving the cords 24, which then spans the distance to the opposite blade 18 where it wraps around a similar radius to the one on blade 16, terminates, and is fixed. The second cord 30 (shown in FIGS. 3A–D) is similarly disposed, but, in the end effector, in a direction opposite to cord 24. Thus, cord 30 extends along the longitudinal axis of barrel tube 6 over a second pulley (not shown, but identical to pulley 26), which is free to rotate independently around pin 20, and along the back of the proximal end of the blade 18. Cord 30 is received by a polished radius machined in the proximal end of blade 18, spans the distance to the opposite blade 16, where it wraps around a radius, is terminated and fixed in place.

FIG. 2B is a cross-sectional view of the scissor-like end effector 8 wherein the blades 16, 18 are closed and aligned with the longitudinal axis (A) of the barrel tube 6. FIG. 2B and 2C illustrate that when the working tip 8 is closed, its diameter is no greater than the diameter of the barrel tube 6. In a preferred embodiment, that diameter is such that the instrument 2 may readily pass through a 5 mm trocar sleeve or a laparoscopic port of only 5 mm (sleeve and port not shown). Thus, versatility and 3-dimensional control of the end effector 8 of the invention is achieved without sacrificing the small diameter required for minimally invasive surgical procedures.

FIGS. 2D and E depict alternative embodiments of the present invention wherein the end effector 8, particularly the jaws or blades 16, 18 thereof, have a different shape. FIGS. 2D and E are numbered commonly with FIGS. 2A–C, and the operational aspects of the alternative tip embodiments of FIGS. 2D and E are identical to that of FIGS. 2A–C.

FIGS. 3A–D show the preferred embodiment of the present invention and depict the 3-dimensional movement available at the working end effector scissor-like tip 8. Each of the two cords 24, 30, extend parallel to the axis of the barrel 6 (line A) and are attached to two nuts 32, 34. The nuts 32, 34 are constrained by appropriate means, such as key or spline, to prevent them from rotating in the barrel tube 6, but to allow their axial movement generally along the axis of the barrel 6. Each cord 24, 30 is attached to its respective nut 32, 34. Thus, cord 30 is directly connected to nut 34, and cord 24 passes through a hole in nut 34 and is connected to nut 32. A shaft 36 extends coaxially along the entire length of barrel tube 6 and is threaded adjacent to its distal end. It is threaded with a standard thread along a length 38 which exceeds the total desired travel of the cords 24, 30 as the end effector 8 is rotated from one extreme to the other. Equal lengths 40, 40' of the shaft 36 are threaded in opposite directions. Rotation of shaft 36 in one direction causes nuts 32, 34 to advance together, and rotation in the other, opposite direction causes nuts 32, 34 to drive apart.

FIG. 3B shows the result of retracting shaft 30 in the proximal direction (i.e., along arrow B toward the handle 4), pulling nuts 32, 34 and, therefore, cords 24, 30 simultaneously. The blades 16, 18 close relative to one another, but without rotation relative to the barrel tube 6. This is an important aspect of the invention 2 because it allows the user to maintain the working end effector tip 8 at a constant angle relative to the axis of the tubular barrel 6, while still achieving activation of the end effector 8. When both blades 16, 18 are closed and straight, as shown in FIG. 3B, the profile of the entire device 2 is within the profile required for passage through a relatively small laparoscopic surgical port or to access a tight area.

FIG. 3C shows the pivoting action (arrow C) of the end effector 8 as a result of rotation of shaft 36. Rotating shaft 36 relative to barrel tube 6 causes nuts 32, 34 to drive together, pulling on cord 30 while releasing cord 24 exactly the same amount. This results in pivoting the end effector 8 in the plane of the axis of the barrel tube 6. It can also be seen that the pivoting of the end effector 8 is independent of the degree of closure of blades 16, 18. That is, the pivoting of blades 16, 18 is independent of how far shaft 36 is retracted in the proximal direction. This is useful because it allows a surgeon to control both closing and pivoting of blades 16, 18 independently, which allows him to selectively separate or cut tissue.

FIG. 3D shows the rotational action of the end effector 8 as a result of simultaneously rotating both shaft 36 and barrel tube 6 (arrows D). When both shaft 36 and tube 6 are rotated in the same direction at the same rate, the nuts 32, 34 do not advance relative to the tube 6 and no pivoting of the end effector 8 occurs. The net result is the simultaneous rotation of the barrel tube 6 and end effector 8 (arrow D'). It can also be seen that closing of the blades 16, 18 is independent of the degree of rotation of the barrel 6 and end effector 8. This mechanism also has the advantage that the system has no orientation preference and the control cords 24, 30 cannot tangle or cross. This advantage is significant for interchangeable end effectors (including the detachable barrel 6 and selected end effector 8), because reattachment (i.e., plugging a selected end effector or barrel into the handle) does not require special orientation or locating of engagement structure.

Referring to FIG. 4, the handle 4 houses the operating mechanism 10. This is an embodiment of the present invention wherein closing the end effector is performed manually by retraction of the finger trigger. The barrel tube 6 is, an integral part of the end effector assembly inserted into a receiving hole in handle 4, and is restrained by a detent 38. The proximal end of barrel tube 6 is forked, or fitted with an appropriate connection mechanism, such as a spline, resulting in positive torsional engagement with gear 40. Gear 40 provides for positive rotational driving of the tubular barrel 6 around its longitudinal axis. The proximal end 42 of shaft 36 is adapted (square or splined) to engage with gear 44, but slide through gear 40 to allow positive rotational driving of shaft 36, independently of gear 40 and the barrel 6. The shaft 36 is biased in the distal direction relative to the barrel 6, i.e., toward the end effector tip 8 by the spring (or springs) 22 integrated with the end effector tip 8. The shaft 36 extends through a collar 45 and is positively connected with it, allowing pulling of collar 45 in the proximal direction to move shaft 36 in the like direction. Collar 45 is biased in the distal direction by a spring 46 and is connected to trigger 48 by a fork assembly 50 which allows free rotation of the shaft 36 and spline 42, but also enables the retraction of shaft 36. Pulling the trigger 48 causes closing of the blades 16, 18, and the amount of closure is directly proportional to the travel of the trigger 48.

Figure 9A:
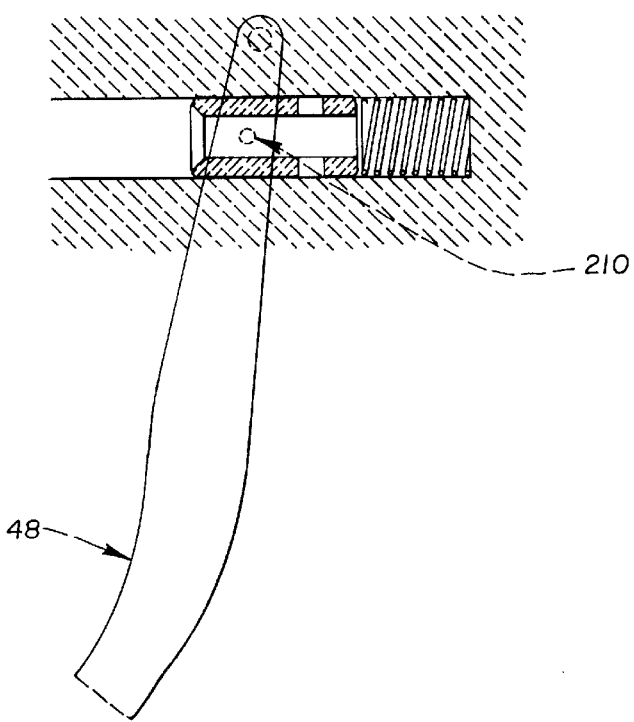
FIG. 9A is a fragmentary cross-section showing the interconnection of the trigger and collar of the embodiment shown in FIG. 9.
Figure 9:
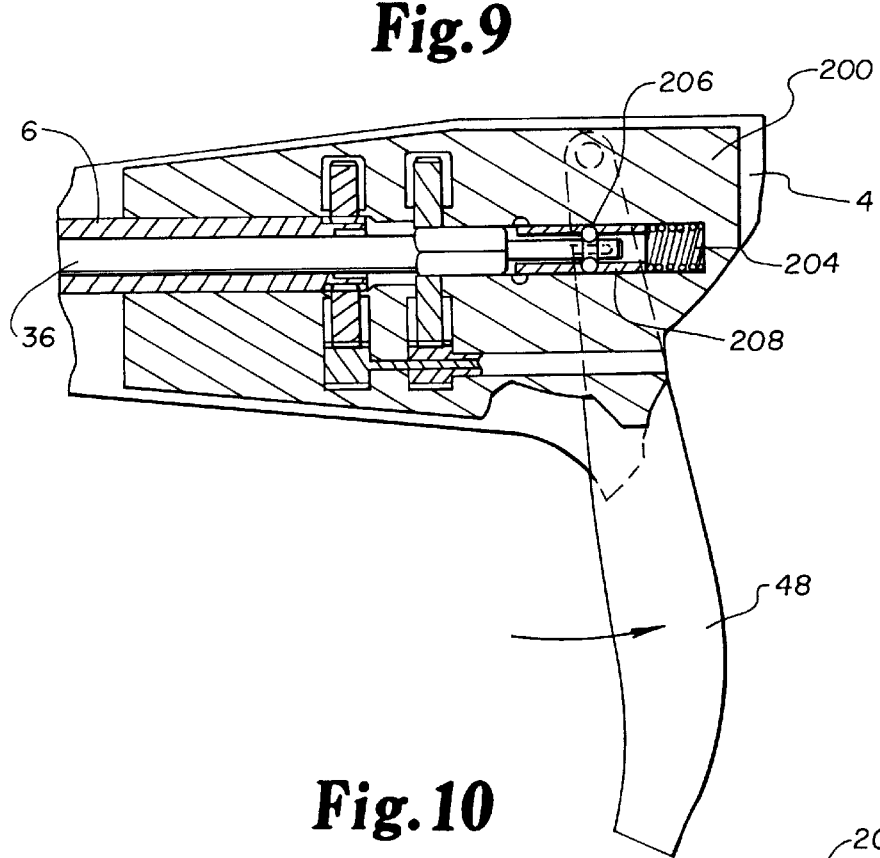
FIG. 9 is a cross-section of a second embodiment of the handle and operating mechanism of the instrument of the present invention.
Figure 10:
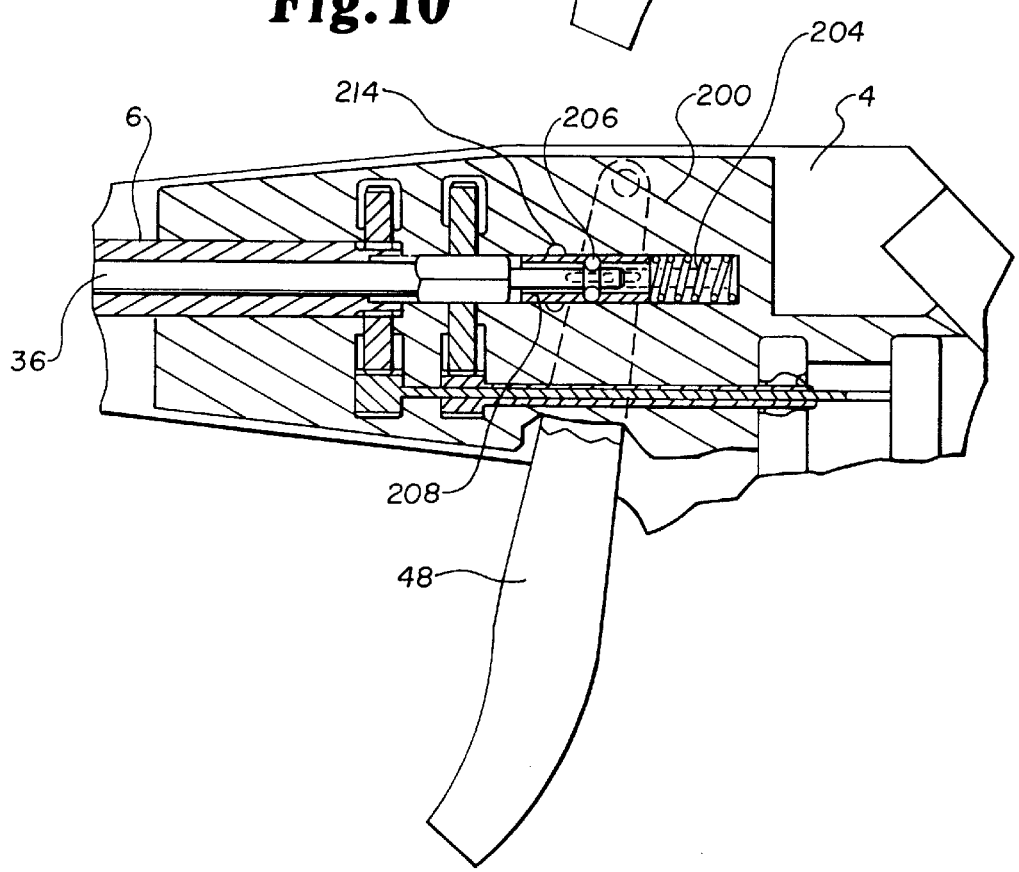
FIG. 10 is a cross-section of the second embodiment depicted in FIG. 9, with the operating trigger in another position.
Figure 11:
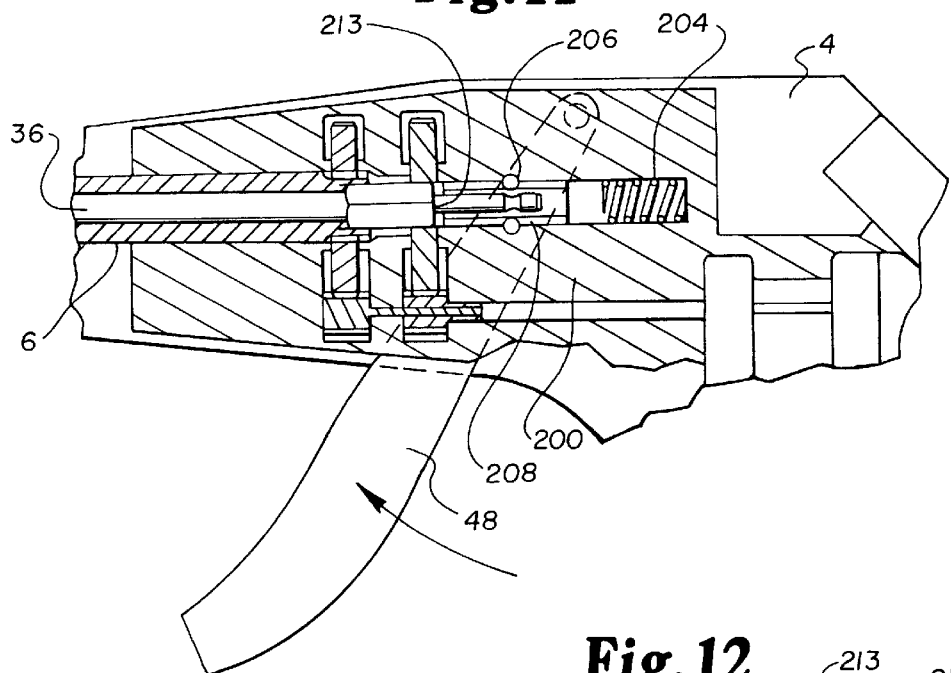
FIG. 11 is a cross-section of the handle depicted in FIGS. 9 and 10, with the operating trigger in a third position.
Figure 12:
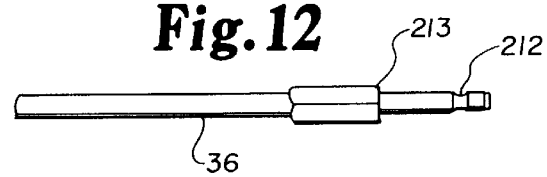
FIG. 12 is an elevational view of the operating shaft of the present invention.

Referring to FIG. 9–12, an alternative embodiment of the present invention is depicted. Specifically, the shaft 36 and barrel 6 are retained in a generally cylindrical locking sleeve 200 rigidly mounted in the handle 4. The sleeve 200 contains, operably and slidably, a spring 204, a set of detent balls 206 captured in a collar 208 and a trigger pin (not shown). The shaft 36 and barrel 6 are held in the handle 4 by the balls 206 which releasably engage in a detent ring 212 adjacent to the proximal end of the shaft 36 (see FIG. 12, depicting more details of the shaft 36, including the splined or square portion thereof), thereby locking the shaft 36 to the collar 208, while allowing the shaft 36 to rotate freely in the sleeve 200. Retraction of the shaft 36, and the resultant closing of the end effector tip 8, is accomplished by moving the trigger 48 in the proximal direction, retracting the collar 208, operably coupled to the trigger by the pin 210 (see FIG. 9A).

With reference to FIG. 11, moving the trigger 48 in the opposite, distal direction, beyond its normal range of travel for opening and closing the end-effector tips 8, enables the barrel and end effector assembly to be removed from the handle 4. This movement of the trigger 48 slides the collar 208 against a shoulder 213 on the shaft 36 (FIG. 12), pushing the barrel 6 and shaft 36 in the distal direction, out of the handle 4. When the trigger 48 is moved to a fully unlocked or release position, the collar 208 is moved in the distal direction until the balls 206 are released radially outwardly into a ball receiving detent ring 214 (best seen in FIG. 10) on the inside of the sleeve 200, freeing the shaft 36, together with the barrel 6 and end effector 8, from the handle 4. Replacing the same, or a different end effector assembly (barrel 6 and tip 8) is accomplished by pushing the new assembly into the handle 4 in the proximal direction.

Referring back to FIG. 4, detent 38 may be used for further securing the barrel tube 6 and the shaft 36 it carries to handle 4. By depressing the detent 38, dog 72 is disengaged, allowing the barrel tube 6 and shaft 36 to be removed from handle 4 as outlined with reference to FIGS. 9–12. In this manner, multiple tip assemblies (including the barrel 6 and a selected end effector) may be used with a single handle 4 and be safely and operably secured to the handle 4.

With continued reference to FIG. 4, gear 40 meshes with gear 60 on a separate shaft 61, driven through separate gear box 56 and motor 58. Gear 44 meshes with gear 52 on a second shaft 54, driven through gear box 62 and motor 64. The two discrete motor and gear assemblies allow, direct control of each independent axis of movement of the end effector 8. The motors 58, 64 are controlled by a multi-positional joystick-type control switch 66 mounted on the handle 4 within comfortable reach of the user's thumb. Power for the motors 58, 64 is supplied by an integral, rechargable or removable battery 68, and power and position are controlled by suitable, commercially available microprocessing control electronics 70.

FIG. 5 shows the control switch 66 mounted on the handle 4. A small label 74 shows the effect of moving the control switch 66 in each respective direction. The switch 66 may be controlled easily with the thumb of one hand, and has the following effects: (i) pushing the switch 66 up (labeled "CW") causes simultaneous clockwise rotation of barrel 6, shaft 36 and end effector 8; (ii) pushing down (labeled "CCW") causes simultaneous counterclockwise rotation of shaft 36, barrel 6 and end effector 8; (iii) pushing the switch 66 left (labeled "Lt") causes pivoting of the end effector 8 to the left by rotating only shaft 36 in the clockwise direction; and (iv) pushing the switch 66 right (labeled "Rt") causes pivoting of the end effector 8 to the right by rotating only shaft 36 in the counterclockwise direction. Movement in this embodiment is discrete and not proportional, although minor modification of control electronics 70 could enable such proportional control.

Figure 13:
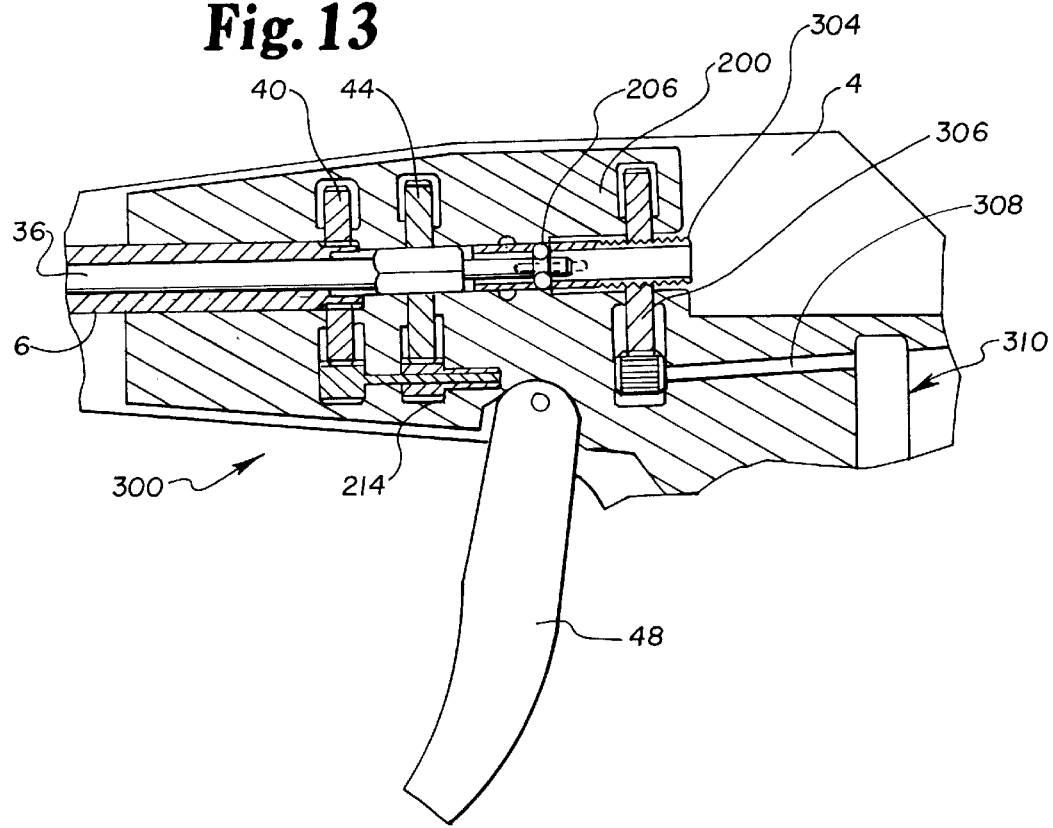
FIG. 13 is a cross-sectional view of a third embodiment of the handle and operating mechanism of the present invention.

Referring to FIG. 13, another handle and operating mechanism embodiment 300 of the present invention is depicted and includes another servo motor indicated generally at 310. The motor operates or drives the automatic, powered "vibra-sector autoclose" function of the end effector tip 8. The motor 310 may be controlled by a microprocessor incorporated into the present invention as outlined below. In FIG. 13, the handle 4, barrel 6, shaft 36, trigger 48, gears 40, 44 and the engagement and release mechanism (including the balls 206, and sleeve 200, shown in FIGS. 9–12) are substantially the same and commonly numbered. The collar 304 is threaded on its outer, generally cylindrical surface and meshes with a complementary threaded gear 306. The gear 306 is driven by a pinion 308, operably coupled to an augmented motor and gearbox drive assembly 310. Driving the gear 306 in one direction, causes the retraction of the collar 304 and shaft 36, closing the end effector tip 8. Driving the gear 306 in the opposite direction moves the collar 304 in the distal direction, pushing the shaft 36 (and the barrel 6) out of the handle 4. Disengagement is accomplished as before, i.e., when the balls 206 are released into the expanded ring in the inside diameter of the sleeve 200.

Although the trigger 48 is substantially the same, in the embodiment 300 shown in FIG. 13, it is basically a multi-position switch biased in the distal direction. At least five positions are provided for controlling the motor 310; each position is indexed, providing tactical or audible feedback to the user. One position, a fully released or open position (position 1), corresponds to a control signal sent to the microprocessor to move the motor 310 at high speed until the end effector tip 8 is fully open and held open. Another position (position 5), the trigger's proximal position, provides a signal to the microprocessor to operate the motor 310 to close the end effector 8 at high speed and hold it closed. Intermediate positions at 25%, 50% and 75% (positions 2, 3 and 4, respectively) of trigger travel correspond to slow opening of the end effector, motor disconnect to fix the end effector in its current position and slow closure of the end effector, respectively. Additionally, the trigger might be adapted to be movable vertically to provide a "lock-out" feature, immobilizing the end effector 8 in any position.

When the trigger 48 is moved off the neutral position, i.e., either pulled or released, the microprocessor may be used to set the voltage to maintain a set speed. If the trigger is held as outlined above, for example in the 75% pulled position, the motor continues to close the end effector until it begins to slow down. At this point the microprocessor 70 automatically increases the voltage and thereby current, to maintain the desired speed. This continues until the motor is stalled at full current, translating to maximum closing force at the end effector. The microprocessor maintains full current on the motor until the motor is driven to the position corresponding to the end effector fully closed. At this point power is removed from the motor. This feature minimizes heat build up in the motor and current drain on the battery, prolonging the time between charges.

For example, assuming the blades or jaws of an end effector are fully open initially, moving the trigger from position 1, through position 2 and into neutral position 3, no blade movement will occur. When position 4 is reached, the blades begin to close slowly and, in position 5, they will close rapidly to full closure. Assuming initially fully closed blades and reversed sequential movement of the trigger, reversed movement of the blades will occur. Thus, for rapid snipping, the trigger is moved rapidly between positions 1 and 5; for slow snipping, the trigger is moved between positions 4 and 2. Beginning with closed blades or jaws enables tissue spreading.

The operational options and parameters of the instrument of the present invention are increased by incorporating the electrical motors and control devices described above. Controlling the additional motors and the additional functions provided by the motors, such as vibration or oscillation of the end effector tip, is facilitated by using a microprocessor 70. This is particularly true when it is desired to include electronically controlled reciprocating movement of the end effector, vibration of the end effector tip, or another complex movement or motion involving coordinated actuation. Additionally, proportional control in one or more directions or dimensions may be a desired attribute. For example, the harder the user pushes on the control button or trigger, the greater force with which the end effector tip closes and opens. Similarly, the harder the user pushes on a switch, the more rapidly the end effector closes or opens. Because of its flexibility, and dedicated control functionality, a microprocessor is particularly well-suited to achieve control of the servo motors for applications such as these. In any of the embodiments disclosed herein, microprocessor 70 may be used to monitor both voltage and current through the drive motors, as well as monitoring and regulating speeds, motor temperatures, and battery charge states.

Figure 24:
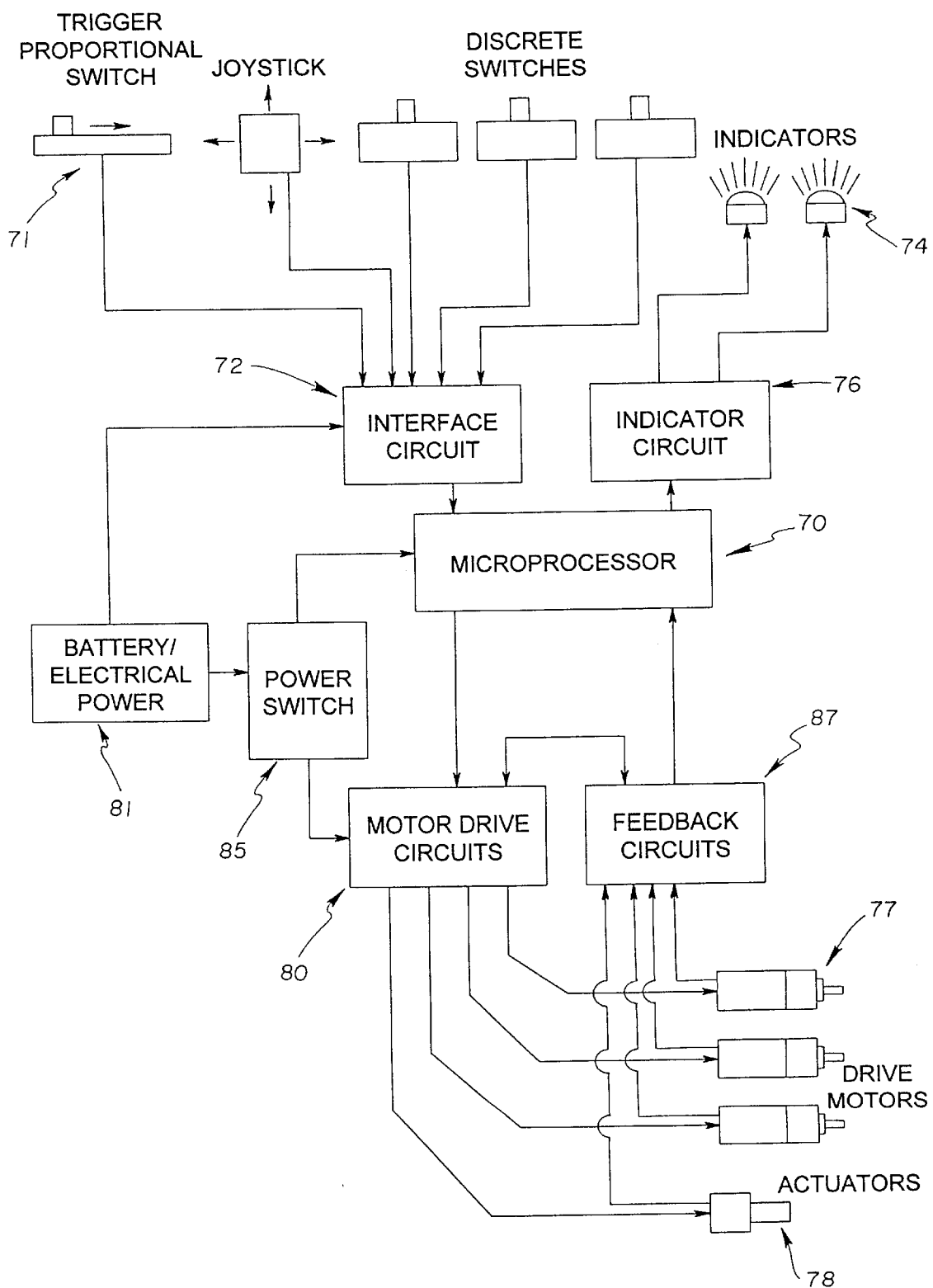
FIG. 24 is a schematic depicting the integration of a microprocessor into the electronic embodiment of the instrument of the present invention.

FIG. 24 is a schematic diagram of a microprocessor controller associated with the surgical instrument of the present invention. Each of the functional blocks may or may not be a discreet functional circuit. Input into the microprocessor, indicated generally at 70, from the operator is through switches, variable resistors, encoders, or other known devices (indicated generally at 71). Depending on the type of component used, the microprocessor may require an interface circuit 72. Similarly, the status indicator lamps 74 may also require some external circuitry 76. The motors or other actuators 78, of course, cannot be driven directly from the microprocessor 70; each requires a drive circuit 80 to regulate the power supply 81 to them. Feedback from the motors or actuators is provided by encoders or limit switches (not shown), controlled by and conditioned by a feedback circuit 87. In some instances, it may be desirable to avoid feedback control, relying instead on a feed forward system (not shown) utilizing, for example, stepper motors instead of servo motors. Electrical power is removed from the device via an electrical switch 85, providing on-off battery connection.

With reference to FIGS. 4 and 24, and the program flow shown in FIGS. 14–23, the present invention incorporates single board computer with microprocessor functionality equivalent to a Motorola 68HC11 processor with a programming language in internal ROM. The control software may be contained in an external EPROM. The 68HC11 processor contains a section of EEPROM which is used to store set points, etc., while the instrument of the present invention is off. The single board computer is operationally coupled to a servo drive control module (80, FIG. 24) containing motion controls IC's (for example, Hewlett-Packard HCTL-1000) which control the multiple drive motors (77, FIG. 24). The selected microprocessor itself may be programmed to perform the servo control functions of the separate motion control IC's. Interfaces (72, FIG. 24) also may be provided to decode the output of the joystick and proportional switches (71, FIG. 24) used by an operator.

Referring to FIGS. 14–23, the software for the instrument of the present invention is composed of a main loop 390 which executes continuously while the instrument is switched on, and several secondary loops (FIGS. 15–23) which control special functions such as reciprocating, cutting or vibration and the like. One primary purpose of the main loop 390 is to query the joystick and other control switches to determine whether an operation is desired. If so, the appropriate subroutine is called. The main loop 390 runs every 20 milliseconds while the instrument is on and may be adapted to check continuously system operating parameters and update the displays, represented in FIGS. 15 and 23, respectively. The only way to exit the main loop 390 is remove power from the instrument.

Motor movement is accomplished by the motor control chips which are run in the positional error mode. Relative and absolute positions are always maintained to assure repeatable movement and an absolute zero reference. The absolute positions are established during the initialization routines (FIG. 15), wherein motors are driven from limit to limit to establish the absolute zero reference point. Each motor movement is measured relative to a target position for that encoder, the position calculated by the microprocessor. The speed is multiplied by a gain factor used to allow a user to control distance sensitivity. If a position error ever exceeds an error limit, which is determined by motor limits during initialization (FIG. 15), then the main control loop 390 infers a component failure, declares an error and lights the appropriate lamp. Special functions such as reciprocating, cutting, vibration, autozero and barrel disengagement are handled in separate routines FIGS. 18–22.

The handling of switch closure and joystick movement is straight forward. Because the movement routines are separate and distinct, the logic for each motor move is separate from another. However, because the main loop 390 executes so rapidly, the motion control ICs will accept destination positions and rates, and because the motors have mechanical inertia, the resulting motor movement is functionally concurrent. This allows simultaneous movement in all three axes. Other operator setable functions such as speed, force, and joystick sensitivity may be programmed by a suitable set of soft keys or dedicated buttons. Information may be displayed through the indicator lights or a display such as an LCD.

Figures 14, 14A:
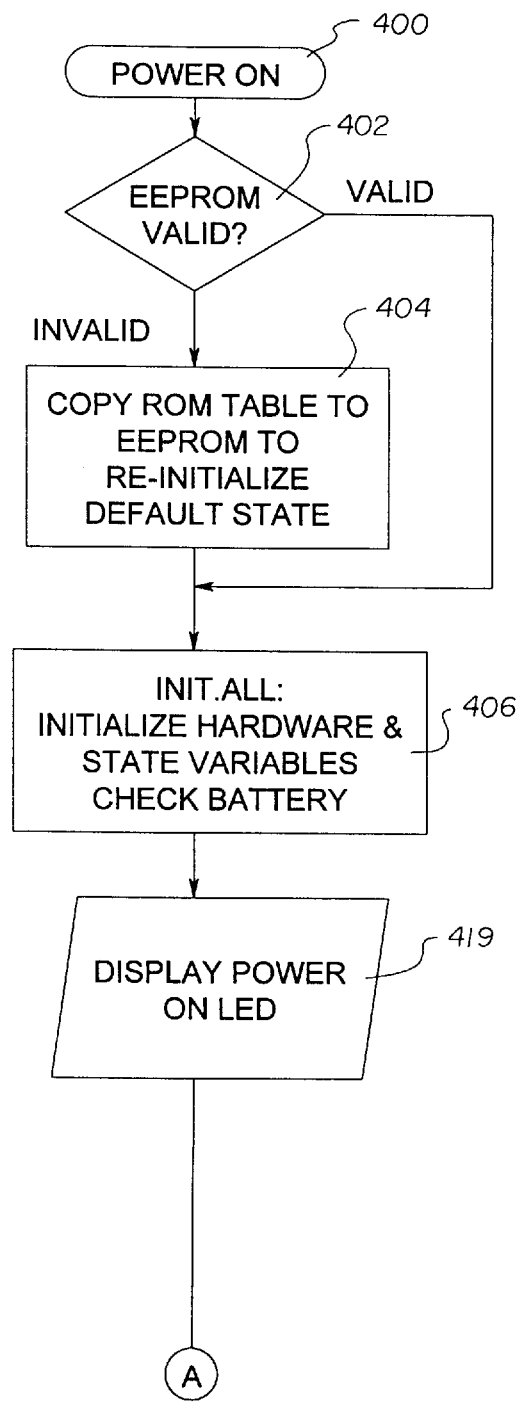
Figure 15:
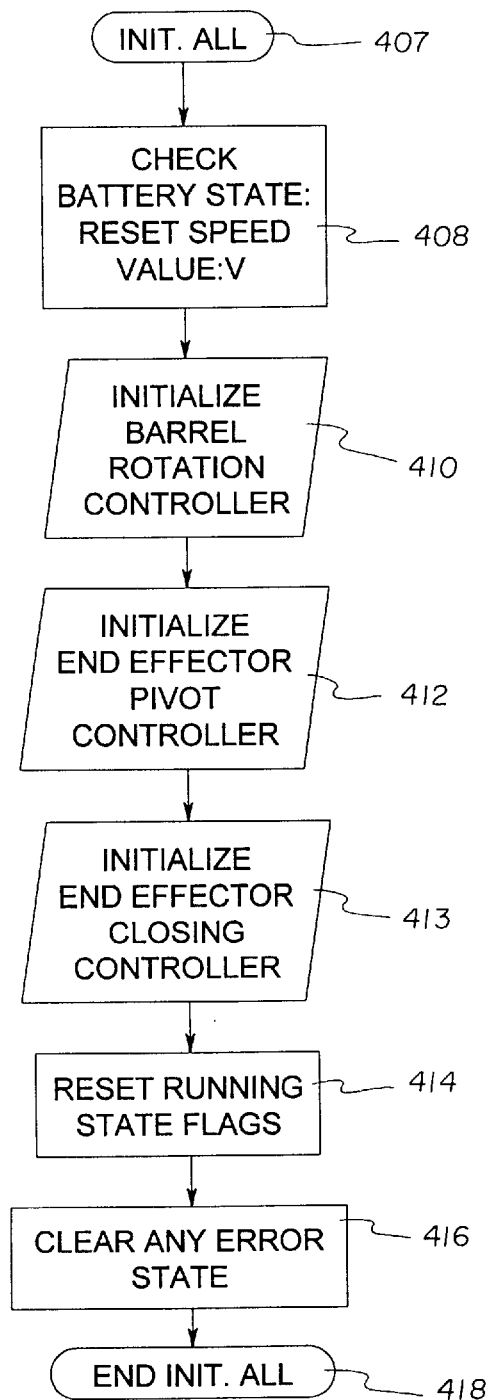

Operation of the instrument 2 of the present invention is broadly depicted by the flow diagram of the main program loop for the microprocessor depicted in FIG. 14. Power is provided to the instrument at block 400. The program proceeds through the EEPROM block 402 and reinitializes at block 404 if there is a default state. Initializing the hardware and stating the variables, as well as checking the battery occurs next at block 406. This operation is set forth in more detail in FIG. 15, beginning with initialize all block 407 and proceeding to the check battery block 408, the barrel rotation controller 410, pivot controller 412, and end effector closing controller 413. The running state flags are reset at block 414 and any error is cleared at block 416. Initializing ends at block 418, at which point the program flows to the display power on block 419 (FIG. 14).

Figure 23:
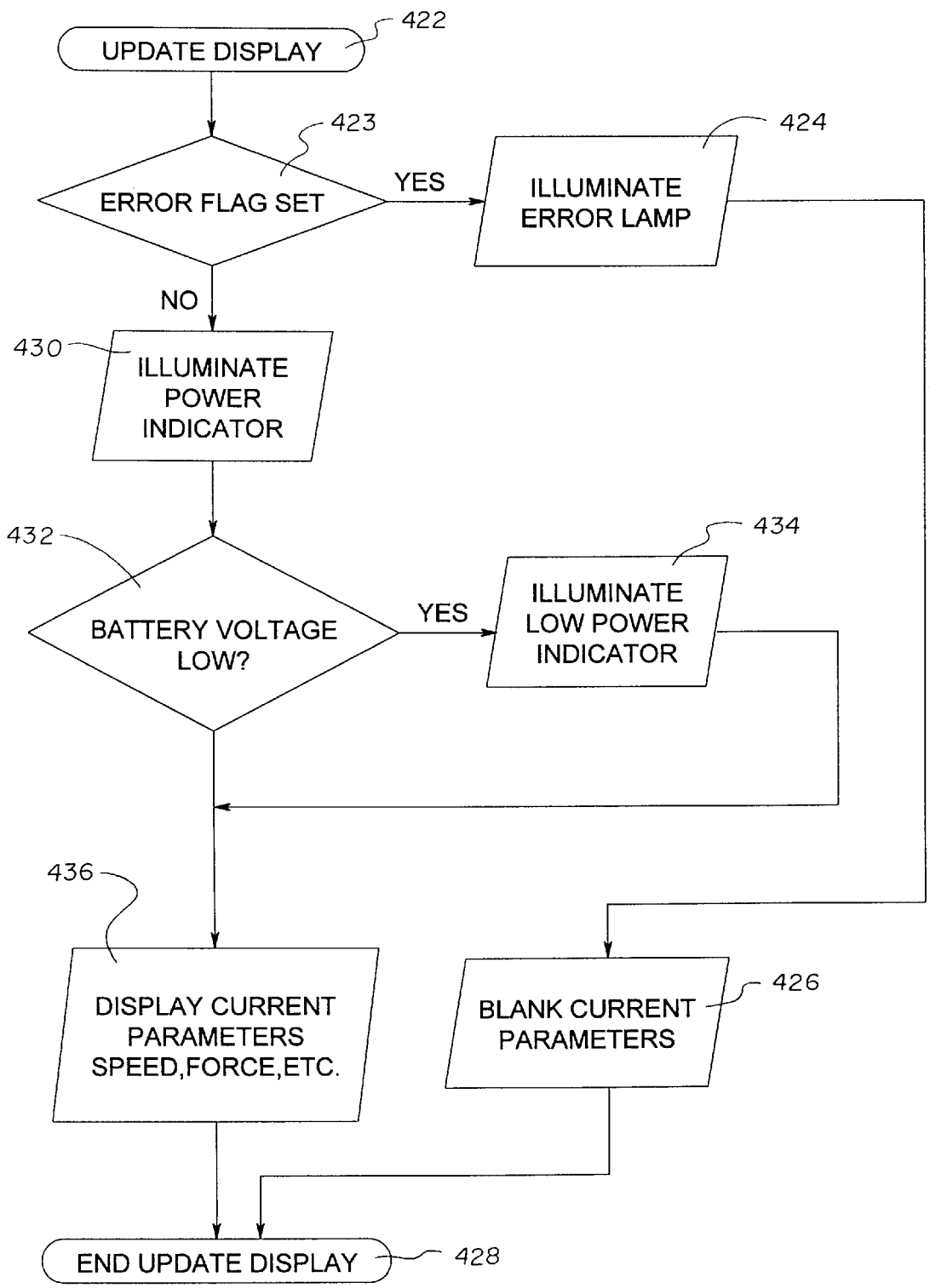

After error query block 420, at block 421 the displays are updated, as shown in FIG. 23, beginning at update display block 422. Initially, the error flag set query is made at block 423 and, if the answer is yes, the error lamp is illuminated as represented at block 424, current parameters are blanked, block 426, and the update display ends at block 428. If there is no error detected at block 423, the power indicators are illuminated, block 430, and a battery voltage query is made, block 432. If voltage is low, the low power indicator is lighted at block 434 and the flow proceeds to display current parameters (including operational parameters such as speed, force, etc.), block 436. At that point, the end display update program is reached at block 428.

Figure 16:
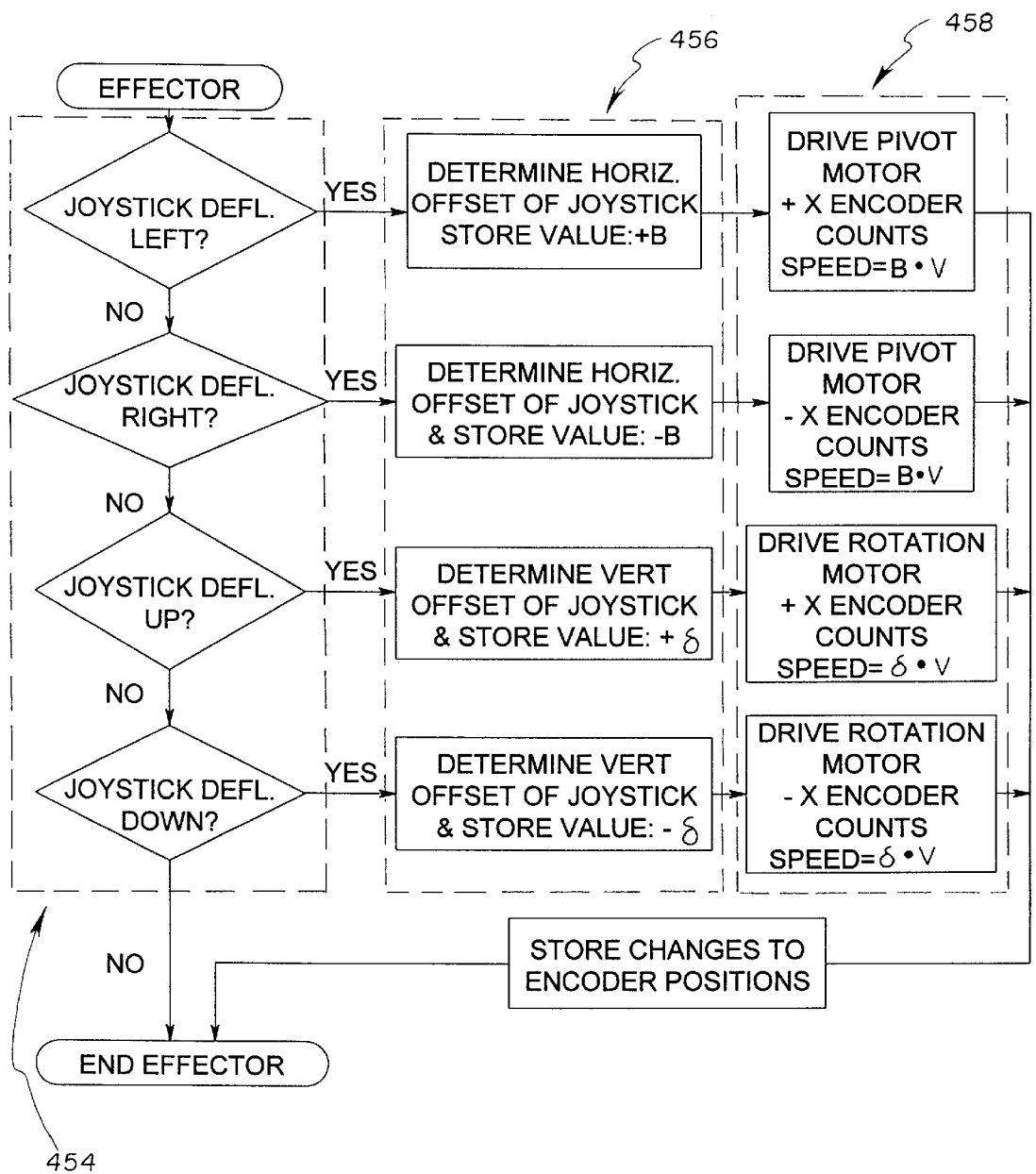

With further reference to FIG. 14, if no errors are detected, use of the instrument may proceed to a specific inputs by the operator and queries by the program, such as the joystick query and movement blocks 450, 452, respectively. Referring to FIG. 16, the program flow controlling effector movement is set forth in more detail as a series of queries and comparisons indicated generally at blocks 454, 456, respectively, and input operational commands indicated generally at block 458.

Figure 17:
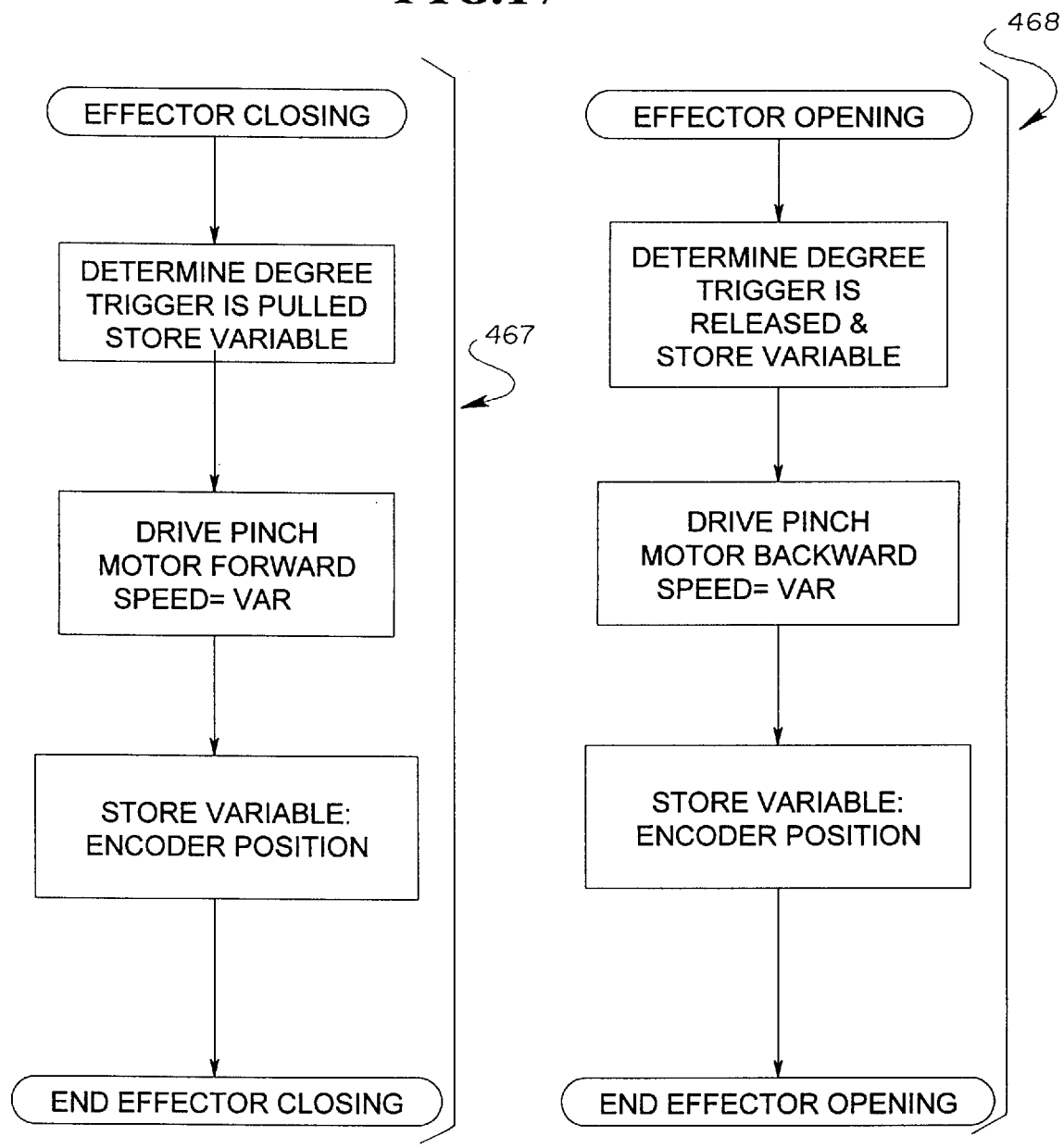

Similarly, the trigger 48 is monitored at the trigger query blocks 460, 462, resulting in effector closure function blocks 464, 465 and 466. FIG. 17 depicts the effector closing and opening sequence in exploded views at blocks 467 and effector opening likewise as exploder block 468, respectively.

Figure 18:
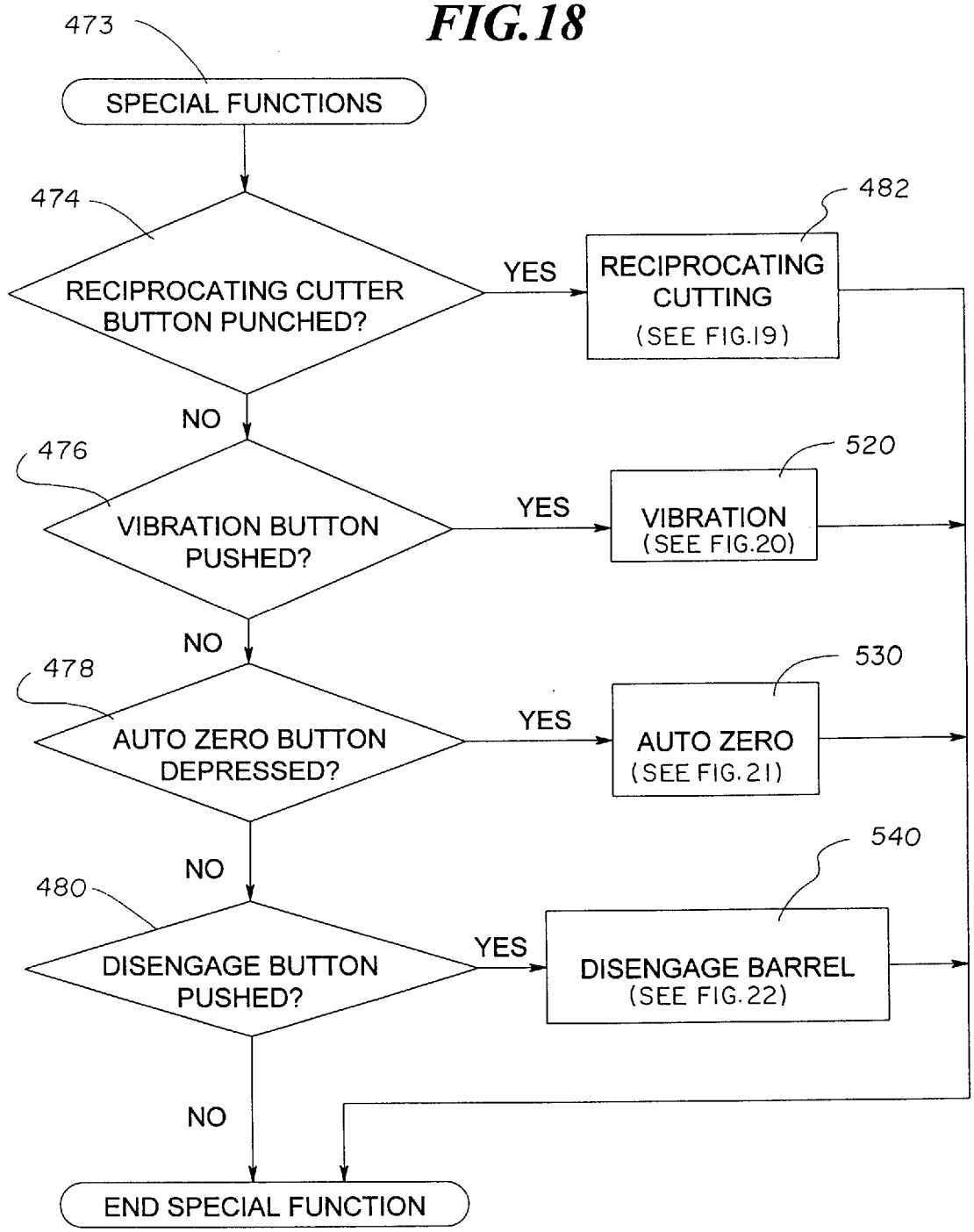
Figure 22:
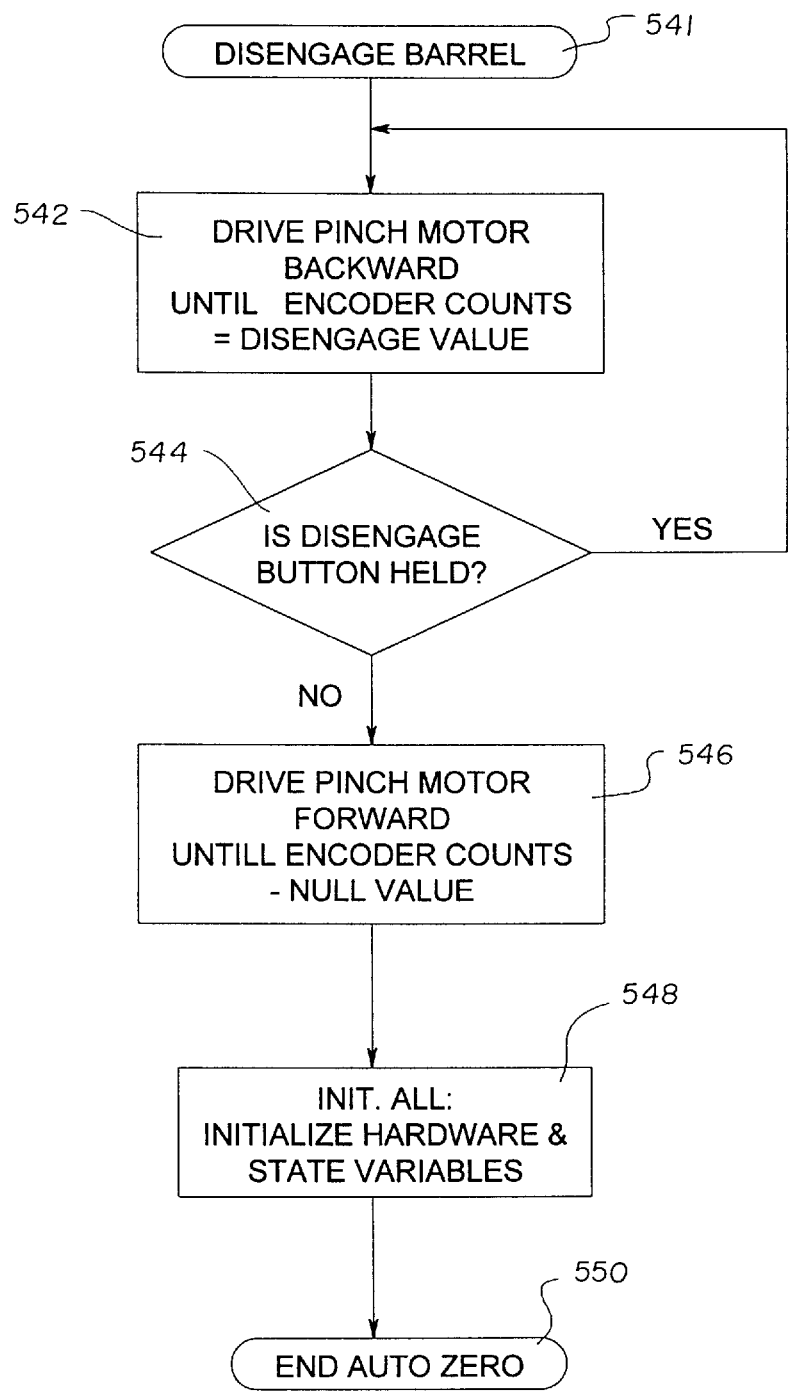

FIG. 14 reflects that the program includes a special function query, block 470, which, if a special function is required and actuated, directs the flow to block 472, set forth in further detail in FIG. 18. Block 473 begins the special functions flow then proceeds to query each of the special functions including reciprocating cutting, block 474, vibration, block 476, autozero, block 478, or the disengage function, block 480. With respect to the reciprocating query, if the answer is positive, flow proceeds to operational reciprocating cutting block 482, shown in more detail in FIG. 19.

Referring to FIG. 19, the reciprocating cutting flow begins at block 483 and first queries whether the function has been requested at block 484. If the answer is no, the flow proceeds to end reciprocating, block 486. If the answer is yes, the motor is driven fully forward, block 488. The flow then proceeds to query whether the end effector is fully closed, block 490. If the answer is no, the program returns to the beginning, and if the answer is yes, a query is made as to whether the request button is still depressed, block 510. A negative response directs the flow to end reciprocating, block 486. If the answer is yes, the motor is operated, block 512, and the end effector is queried, block 514. If the answer is yes, the program returns to the beginning and, if the answer is no, a query is made as to whether the end effector is fully opened, block 516. If the answer is no, the program returns to the start point until the fully open state is reached.

Referring back to FIG. 18, the vibration query at block 476 leads to the vibration function, block 520, shown in further detail in FIG. 20. Upon actuation of the vibration request, block 521, the flow proceeds to drive the pinch motor, either forward, block 522, or backward, block 524. The program then queries whether the operating request button is still depressed, block 526; if the answer is yes, flow returns to the start, and if no, the vibration flow ends, block 528.

Again referring back to FIG. 18, the special functions include the autozero query, block 478. If answered positively, the flow proceeds to autozero function, block 530, set forth in further detail in FIG. 21. Flow at block 531 and, if actuated, the program drives the pivot motor forward/backward until a null value is reached, block 532. Similarly, the pinch motor and rotational motor are driven until null values are reached respectively, blocks 534, 536, and autozero ends, block 538.

Returning to FIG. 18, another query in the special function begins at the disengaged query block 480. If the answer is yes, the flow proceeds to block 540, to disengage the barrel as set forth in FIG. 22. This function flow begins at block 541. Next, the pinch motor is operated to equal the disengage value, block 542. At that point, the program queries whether the disengage button is still depressed, block 544, and if the answer is yes, the program returns to drive block 542. If the answer is no, the pinch motor is driven forward until a null value is reached, block 546, and the program flows to an initial all block 548 wherein the hardware is reinitialized and variables stated, reaching the end of the autozero program, block 550. The main program flow (FIG. 14) also includes a periodic check system function, block 560.

FIGS. 6A–B, 7A–D and 8A–B show alternative embodiments of the scissor-like end effector tip 8, depicted in FIG. 2A–C. FIG. 6 shows an end effector 9 similar to that shown in FIG. 2A. The two blades 80, 82 are closed by a pair of cords (not shown) in a manner identical to that described above with reference to FIG. 2A. The principal difference in the two designs is that another pair of cords 84, 86 (only cord 84 is shown) are used to open the blades 80, 82 instead of relying on a spring 22 to bias them open, and blades 80, 82 have levers 81, 83. Cord 84 extends axially down barrel tube 6, wraps around pulley 26, along the backside lever of the lever on blade 82 and connects to the lever on blade 80. Pulling on cord 84 pulls the levers together, spreading open the blades 80, 82. One advantage is that the cords 84, 86 enable positive opening of the blades 80, 82 such opening may be accomplished with greater force than is possible with spring alone.

Figure 7C:
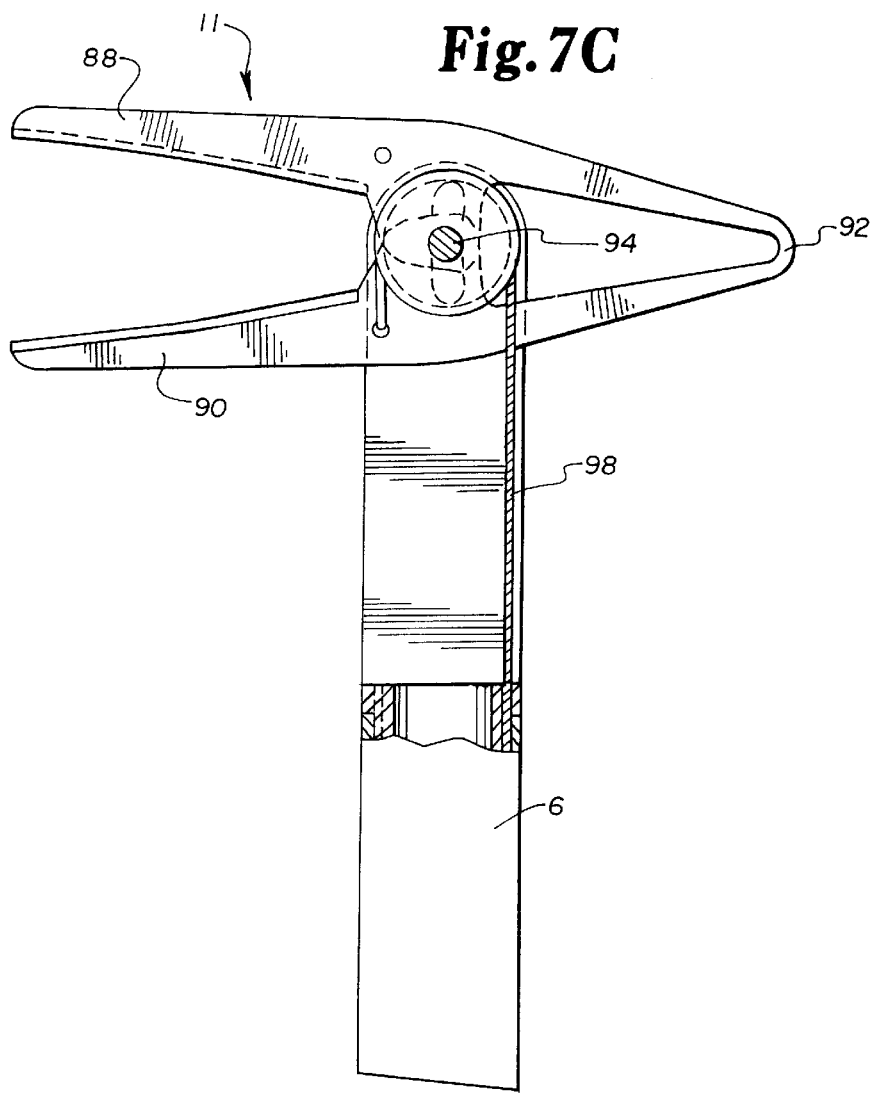
FIG. 7C is a view similar to that of FIG. 7B, depicting rotational movement.
Figure 7D:
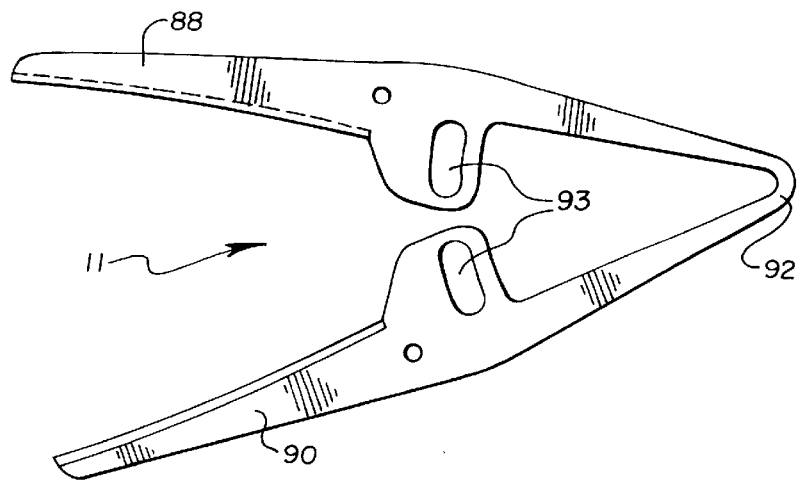
FIG. 7D is a detail side elevation view of the end effector depicted in FIGS. 7A–C.

FIGS. 7A–D shows an alternative scissor-like tip embodiment 11 which offers the same advantages as the scissor-like design shown in FIG. 2A. FIG. 7A shows two shear blades 88, 90 which are ground to shear against one another. They are biased into the open position (FIG. 7A) by an integral spring 92 which connects the blades 88, 90 together. Each of the blades 88, 90 has a slot 93 through which pin 94 passes. The blades or jaws 88, 90 are located by pulley 96 and its "tail" 97 which protrudes in the proximal direction into the bend of the spring 92. The pulley 96 and "tail" 97 rotate together around pin 94 fixed in the end of the tubular barrel 6. This rotation causes pivoting of the blade assembly around pin 94. Cord 98 wraps around the pulley 96 on one side of the pair of blades 88, 90 and attaches to blade 88, 90 on the opposite side. Similarly, another cord 100 runs in the opposite direction around the other pulley (96' in FIG. 7B) and attaches to the opposite blade. Just as illustrated in FIG. 2, pulling on one cord while releasing the other causes rotation of the blades 88, 90 in that direction. FIG. 7C shows the blades 88, 90 rotated 90° (one cord, the far cord, is hidden). Pulling on both cords simultaneously causes closure of the blades 88, 90 and generates a cutting or shearing action. The advantage of this design is that the spring 92 biasing the blades 88, 90 open is an integral part of the blades 88, 90 and, thus, there are only two moving parts (excluding the cords 98, 100) in this embodiment of the end effector 11. FIG. 7D shows the coupled jaws or blades 88, 90, and the spring region 92 coupling them, as well as the slot 93 in each blade.

Figure 8A:
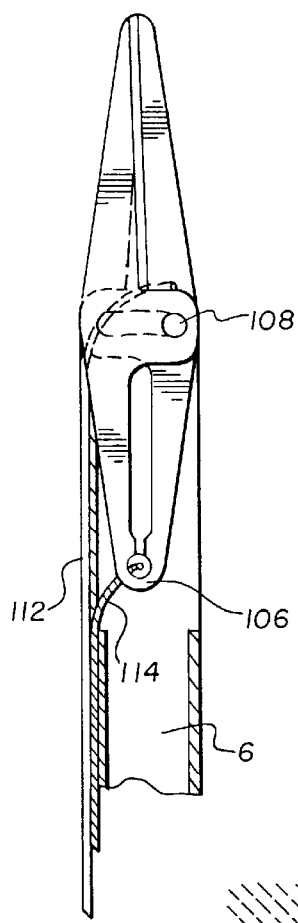
FIG. 8A is a fragmentary view of the distal end of a fifth alternate form of the invention with parts broken away.
Figure 8B:
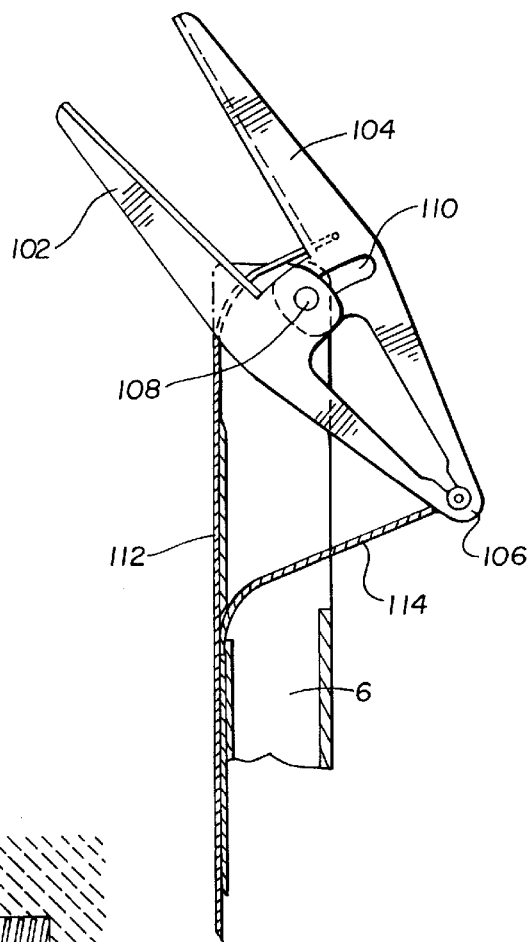
FIG. 8B is a view of the subject of FIG. 8A shown rotated 45 degrees.

FIGS. 8A–B depict a variation of the embodiment illustrated in FIGS. 7A–D. In this version, the blades 102, 104 are attached via integral spring 106. Blade 102 is free to pivot around pivot pin 108 at a discrete point. Pivot pin 108 is fixed in tubular barrel 6. Blade 104 slides closed over blade 102 and has a curved slot 110 to allow movement relative to pivot pin 108. Closure of blade 104 relative to blade 102 is accomplished by pulling on cord 112 which passes over a pulley (not shown). Tension in cord 112 causes the blade assembly 102, 104 to rotate in the counterclockwise direction. This reaction is constrained by cord 114 which holds the angle of the jaws 102, 104 constant relative to axis of the tube 6. Pulling cord 112 while holding cord 114 in fixed position causes closure of blades 102, 104, and a shearing action. A principal advantage of this embodiment is the elimination of indeterminacy characteristic of a spring design without a discrete pivot point.

The instrument of the present invention described herein above is designed particularly for endoscopic use. However, there are many other applications for this invention. For example, the interchangeable tips and operating linkages of the present invention may be incorporated into surgical instruments such as needle holders, staplers, cautery, lasers, balloon catheters, atherectomy devices, or endoscopes. Placement of catheters such as pacemaker leads, pulmonary monitoring catheters (Swan-Ganz type), angiographic catheters, etc. could be facilitated by using the present invention. Additionally, a chip camera could be added to the end effector tip to visualize placement, particularly for the placement of stents and stent graft combinations.

In the embodiment of the present invention shown in FIG. 13, wherein it includes a third motor 310 to operate the end effector tip 8, the trigger 48 could be replaced or augmented by an electro-mechanical switch or a mechanical button operator, e.g., control switch 66 could be adapted to provide control of the third motor 310.

While specific embodiments of the present invention have been disclosed and described, it will be understood by those skilled in the art that various changes in form and detail may be made without departing from the spirit and scope of the invention.

We claim:

1. A surgical apparatus comprising:
    a tubular member with no joints and having a distal end and a proximal end;
    an end effector attached directly to the distal end of said tubular member at an attachment point, the end effector comprising a first pivotable working portion and a second pivotable working portion, the two working portions each extending from the attachment point and forming an operating angle therebetween;
    a handle attached to the proximal end of the tubular member, the handle comprising:
        an elongated grip portion having a longitudinal axis that extends at an angle relative to the longitudinal axis of the tubular member, wherein the grip portion is permanently fixed with respect to the longitudinal axis of the tubular member and grippable by a single hand;
        an actuating control; and
        a pivot control, the actuating and pivot controls being actuable by the same hand which grips the grip portion; and
    linkage extending through the tubular member, the linkage operably connecting the actuating control and the pivot control with the first and second end effector working portions, wherein:
        in response to the actuating control being actuated, the linkage acts on the end effector to alter the operating angle; and
        in response to the pivot control being actuated while the actuating control is not being actuated, the linkage acts on the end effector to pivot the working portions simultaneously in the same direction about the attachment point while maintaining a substantially constant operating angle.

2. The surgical apparatus of claim 1, wherein the handle further comprises a rotate control for rotating the end effector relative to the handle.

3. The surgical apparatus of claim 2, wherein the pivot control and the rotate control include an electric motor driven by stored electrical energy.

4. The surgical apparatus of claim 3, wherein the pivot control and the rotate control include a microprocessor.

5. The surgical apparatus of claim 4, wherein said altering of the operating angle of the end effector working portions is manually controlled.

6. The surgical apparatus of claim 3, wherein the source of the stored electrical energy is associated with the handle.

7. The surgical apparatus of claim 2, wherein the end effector is rotatable 360° relative to the axis of the tubular barrel and is operational in any position relative to the axis.

8. The surgical apparatus of claim 1, wherein the linkage includes two lengths of high-modulus tensile cords.

9. The surgical apparatus of claim 8, wherein said two cords are operably coordinated to provide said altering of the operating angle and said simultaneous pivoting of the end effector working portions.

10. The surgical apparatus of claim 9, wherein the linkage further includes two additional cords for opening the end effector portions relative to one another.

11. The surgical apparatus of claim 1, wherein the tubular member is removeably coupled to the handle.

12. The surgical apparatus of claim 1, wherein the first and second end effector working portions are pivotable through and functional in a 360° included angle.

13. The surgical apparatus of claim 1, wherein the end effector is a scissors.

14. A surgical instrument for use in endoscopy comprising:
    a tubular member with no joints and having a proximal end and a distal end;
    an end effector attached directly to the distal end of the tubular member at an attachment point, the end effector comprising a first pivotable working portion and a second pivotable working portion, the two working portions each extending from the attachment point and forming an operating angle therebetween;
    a handle releasably and rotatably attached to the proximal end of the tubular member, the handle comprising:
        an elongated grip portion having a longitudinal axis that extends at an angle relative to the longitudinal axis of the tubular member, wherein the grip portion is permanently fixed with respect to the longitudinal axis of the tubular member and grippable by a single hand;

an actuating control; and a pivot control, the actuating and pivot controls being actuable by the same hand which grips the grip portion; and linkage extending through the tubular member, the linkage operably connecting the actuating control and the pivot control with the first and second end effector working portions, wherein:

in response to the actuating control being actuated, the linkage acts on the end effector to alter the operating angle; and in response to the pivot control being actuated while the actuating control is not being actuated, the linkage acts on the end effector to pivot the working portions simultaneously in the same direction about the attachment point while maintaining a substantially constant operating angle.

15. The instrument according to claim 14, wherein the linkage comprises elongated, flexible members.

16. A surgical instrument comprising:

a handle with an elongated grip portion grippable by a single hand;

a generally tubular barrel with no joints and having a first end and a second end, the first end being rotatably and releasably coupled to the handle, the grip portion of the handle having a longitudinal axis that extends at an angle relative to the longitudinal axis of the tubular member, wherein the grip portion is permanently fixed with respect to the longitudinal axis of the tubular barrel;

a scissor-like working end effector tip having two pieces, each piece being pivotally connected directly to the second end of the barrel at a common attachment point and having a working portion extending generally distally from the attachment point and a lever portion extending generally proximally from the attachment point;

elongated linkage members extending generally toward the handle, the linkage members including:

a first linkage member attached to the first end effector piece and crossing around the lever portion of the first end effector piece to the lever portion of the second end effector piece and over a pulley on one side of the two end effector pieces; and a second linkage member attached to the second end effector piece and crossing around the lever portion of the second end effector piece to the lever portion of the first end effector piece and over a second pulley on the opposite side of the two end effector pieces;

an actuating control carried by the handle and actuable by the same hand which grips the grip portion, wherein actuation of the actuating control translates both the first and the second linkage members simultaneously in the same direction to pivot the end effector working portions relative to one another; and a pivot control carried by the handle and actuable by the same hand which grips the grip portion, wherein actuation of the pivot control translates both the first and the second linkage members simultaneously in opposite directions to pivot the end effector working portions simultaneously in the same direction about the attachment point, and wherein, a substantially constant angle between the end effector working portions is maintained during the actuation of the pivot control if the actuating control is not also being actuated.

17. The surgical instrument according to claim 16, wherein the pivot control includes a microprocessor, logic and an electrically powered motor.

18. The surgical instrument according to claim 16, wherein the actuating control includes a trigger.

19. The surgical instrument according to claim 16, wherein said end effector is connected to said tubular member so that said end effector may pivot 360° with respect to said tubular member.

20. The surgical instrument according to claim 19, wherein said elongated members are tensile.

21. A surgical apparatus comprising:

a tubular member having a distal end and a proximal end, an end effector movably attached to the distal end and a handle attached to the proximal end;

means for rotating, pivoting and closing the end effector in any orientation relative to the tubular member including lengths of high-modulus tensile cords, a slidable, rotatable shaft with right- and left-handed threaded portions, said shaft being slidable and rotatable relative to the tubular member, two nuts operably received on the shaft and being slidable and non-rotating relative to the tubular member, and means for retracting the shaft in the proximal direction; and means for controlling said means for rotating, pivoting and closing.

22. The surgical apparatus according to claim 21, said means for controlling including a microprocessor.

23. The surgical apparatus according to claim 21, wherein said means for rotating, pivoting and closing includes two of said cords and wherein said cords are operably coordinated to provide said rotating, pivoting and closing.

24. The surgical apparatus according to claim 21, wherein said pivoting and closing takes place about a single pivot point.

25. A surgical instrument comprising:

a handle;

a generally tubular barrel having a first end and a second end, the first end being moveably and releasably coupled to the handle;

a scissor-like working end effector tip pivotally coupled to the second end of the barrel and having two blades pivotally connected to the second end, each blade having a distal end and a proximal portion, the blades crossing over one another at a pivot point generally between the distal end and the proximal portion;

elongated linkage members including a first linkage member attached to the first blade and crossing around the proximal portion of the first blade to the proximal portion of the second blade and over a pulley on one side of the two blades, and a second linkage member attached to the second blade and crossing around the proximal portion of the second blade to the proximal portion of the first blade and over a second pulley on the opposite side of the two blades, said linkage members extending generally toward the handle;

a shaft received in the tubular barrel and being threaded in one direction adjacent to one end and in the opposite direction adjacent to the other end, two nuts received on the shaft, one of the nuts received on each threaded portion of the shaft, the nuts being constrained from rotating and slideable inside the barrel, one of said linkage members being connected to one nut, the second linkage member being connected to the second nut; and actuating means carried by the handle for operating the blades, said linkage members operably coupled to the actuating means.

26. The surgical instrument according to claim 25, wherein the length of the threaded portions of the shaft exceed the travel of the linkage members.

27. The surgical instrument according to claim 26, each proximal portion of the blades carrying a groove to receive a tensile member.

28. The surgical instrument according to claim 27 and a compression spring generally between and biasing the blades apart.

29. The surgical instrument according to claim 28, wherein pulling one of the linkage members while releasing the other pivots the blades in unison, wherein pulling the linkage members simultaneously closes the blades, and wherein rotating the tubular barrel relative to the handle rotates the blades and linkage members.

30. The surgical instrument according to claim 29, wherein said end effector is connected to said tubular member so that said end effector may pivot 360° with respect to said tubular member.

31. The surgical instrument according to claim 30, wherein said elongated members are tensile.

32. A surgical apparatus comprising:
   a tubular member with no joints and having a distal end and a proximal end;
   an end effector attached directly to the distal end of the tubular member at an attachment point, the end effector comprising a first pivotable working portion and a second pivotable working portion, the two working portions each extending from the attachment point and forming an operating angle therebetween;
   a handle attached to the proximal end of the tubular member, the handle comprising:
     an elongated grip portion having a longitudinal axis that extends at an angle relative to the longitudinal axis of the tubular member, wherein the grip portion is permanently fixed with respect to the longitudinal axis of the tubular member and grippable by a single hand to maintain stability of the surgical apparatus during its operation;
     an actuating control; and
     a pivot control, the actuating and pivot controls being independent of one another and further being actuable by the same hand which grips the grip portion; and
   linkage extending through the tubular member, the linkage operably connecting the actuating control and the pivot control to the first and second end effector working portions, wherein:
     in response to the actuating control being actuated, the linkage acts on the end effector to alter the operating angle; and
     in response to the pivot control being actuated while the actuating control is not being actuated, the linkage acts on the end effector to pivot the end effector working portions about the attachment point simultaneously in the same direction while maintaining a substantially constant operating angle.

33. The surgical apparatus of claim 32, wherein, in response to the actuating control being actuated, the linkage pivots both of the end effector working portions either toward one another or apart from one another.

34. The surgical apparatus of claim 32, wherein the handle further comprises a rotate control actuable by the same hand which grips the grip portion, the rotate control for rotating the end effector relative to the handle.

* * * * *